(12) United States Patent  
Pevler

(10) Patent No.: US 9,539,408 B2
(45) Date of Patent: Jan. 10, 2017

(54) NEBULIZER APPARATUS

(71) Applicant: Trudell Medical International, London (CA)

(72) Inventor: Jennifer Pevler, London (CA)

(73) Assignee: Trudell Medical International, London (CA)

( * ) Notice: Subject to any disclaimer, the term of this patent is extended or adjusted under 35 U.S.C. 154(b) by 285 days.

(21) Appl. No.: 14/067,651

(22) Filed: Oct. 30, 2013

(65) Prior Publication Data

US 2014/0116427 A1    May 1, 2014

Related U.S. Application Data

(60) Provisional application No. 61/720,678, filed on Oct. 31, 2012.

(51) Int. Cl.

| | | |
|---|---|---|
| *B05B 1/26* | (2006.01) | |
| *A61M 16/00* | (2006.01) | |
| *A61M 11/00* | (2006.01) | |
| *A61M 16/14* | (2006.01) | |
| *A61M 11/06* | (2006.01) | |

(52) U.S. Cl.
CPC ............. *A61M 16/14* (2013.01); *A61M 11/06* (2013.01); *A61M 2206/14* (2013.01)

(58) Field of Classification Search
CPC .... A61M 16/14; A61M 11/00; A61M 11/002; A61M 11/001; A61M 11/08
See application file for complete search history.

(56) References Cited

U.S. PATENT DOCUMENTS

| | | |
|---|---|---|
| 2,535,844 A | 12/1950 | Emerson |
| 2,882,026 A | 4/1959 | Eichelman |
| | (Continued) | |

FOREIGN PATENT DOCUMENTS

| | | |
|---|---|---|
| EP | 0 261 649 B2 | 9/1987 |
| EP | 0 587 380 | 3/1993 |
| | (Continued) | |

OTHER PUBLICATIONS

PCT International Search Report from PCT/IB2013/002419 dated Mar. 24, 2014.

(Continued)

*Primary Examiner* — Bradley Philips
*Assistant Examiner* — Victoria Leszczak
(74) *Attorney, Agent, or Firm* — Brinks Gilson & Lione

(57) ABSTRACT

A nebulizer includes a housing having a chamber for holding an aerosol, an air outlet communicating with the chamber for permitting the aerosol to be withdrawn from the chamber, and a reservoir for holding a liquid to be aerosolized. The nebulizer also includes a liquid orifice located in the chamber, one or more liquid channels defined between the reservoir and the liquid orifice, the one or more liquid channels having a liquid volume, and a pressurized gas outlet located in the chamber adjacent to the liquid orifice. A baffle is located in the chamber and positioned relative to the pressurized gas outlet and the liquid outlet so as to divert pressurized gas from the pressurized gas outlet and over the liquid orifice. The baffle has a diverter surface area. The liquid volume is at least 80 mm$^3$. The diverter surface area is less than 5.0 mm$^2$.

17 Claims, 17 Drawing Sheets

(56) References Cited

U.S. PATENT DOCUMENTS

| | | |
|---|---|---|
| 3,001,524 A | 9/1961 | Maison et al. |
| 3,269,665 A | 8/1966 | Cheney |
| 3,467,092 A | 9/1969 | Bird et al. |
| 3,490,697 A | 1/1970 | Best, Jr. |
| 3,580,249 A | 5/1971 | Takaoka |
| 3,584,621 A | 6/1971 | Bird |
| 3,630,196 A | 12/1971 | Bird |
| 3,658,059 A | 4/1972 | Steil |
| 3,664,337 A | 5/1972 | Lindsey et al. |
| 3,762,409 A | 10/1973 | Lester |
| 3,826,255 A | 7/1974 | Havstad et al. |
| 3,838,686 A | 10/1974 | Szekely |
| 3,874,379 A | 4/1975 | Enfield et al. |
| 3,990,442 A | 11/1976 | Patneau |
| 4,093,124 A | 6/1978 | Morane et al. |
| 4,094,317 A | 6/1978 | Wasnich |
| 4,106,503 A | 8/1978 | Rosenthal et al. |
| 4,116,387 A | 9/1978 | Kremer, Jr. et al. |
| 4,746,067 A | 5/1988 | Svoboda |
| 4,951,659 A | 8/1990 | Weiler et al. |
| 5,054,477 A | 10/1991 | Terada et al. |
| 5,209,225 A | 5/1993 | Glenn |
| 5,235,969 A | 8/1993 | Bellm |
| 5,312,046 A | 5/1994 | Knoch et al. |
| 5,503,139 A | 4/1996 | McMahon et al. |
| 5,533,497 A | 7/1996 | Ryder |
| 5,533,501 A | 7/1996 | Denyer |
| 5,687,912 A | 11/1997 | Denyer |
| 5,823,179 A | 10/1998 | Grychowski et al. |
| 6,044,841 A | 4/2000 | Verdun et al. |
| 6,129,080 A | 10/2000 | Pitcher et al. |
| 6,131,568 A | 10/2000 | Denyer et al. |
| 6,450,163 B1 | 9/2002 | Blacker et al. |
| 6,612,303 B1 | 9/2003 | Grychowski et al. |
| 6,796,513 B2 | 9/2004 | Fraccaroli |
| 6,929,003 B2 | 8/2005 | Blacker et al. |
| 7,051,731 B1 | 5/2006 | Rogerson |
| 7,270,123 B2 | 9/2007 | Grychowski et al. |
| RE40,591 E | 12/2008 | Denyer |
| 7,568,480 B2 | 8/2009 | Foley et al. |
| 7,581,718 B1 | 9/2009 | Chang |
| 7,634,995 B2 | 12/2009 | Grychowski et al. |
| 7,954,487 B2 | 6/2011 | Grychowski et al. |
| 8,113,194 B2 | 2/2012 | Boehm et al. |
| 8,333,190 B2 | 12/2012 | Addington et al. |
| 8,342,171 B2 | 1/2013 | Boehm et al. |
| 8,347,878 B2 | 1/2013 | Schuschnig et al. |
| D680,214 S | 4/2013 | Eckstein et al. |
| 8,596,264 B2 | 12/2013 | Sommer |
| 9,022,023 B2 | 5/2015 | Korneff |
| 2002/0020762 A1 | 2/2002 | Selzer et al. |
| 2003/0089366 A1 | 5/2003 | Sommer |
| 2003/0136399 A1 | 7/2003 | Foley et al. |
| 2003/0197068 A1 | 10/2003 | Abate |
| 2003/0209238 A1* | 11/2003 | Peters ............... B05B 1/3436 128/200.14 |
| 2005/0145243 A1 | 7/2005 | Trombi |
| 2007/0068513 A1 | 3/2007 | Kreutzmann et al. |
| 2007/0289590 A1 | 12/2007 | Kreutzmann et al. |
| 2008/0230053 A1* | 9/2008 | Kraft ............... A61M 11/06 128/200.23 |
| 2011/0137290 A1* | 6/2011 | Flickinger ............ A61M 11/06 604/514 |
| 2011/0209700 A1 | 9/2011 | Kreutzmann et al. |
| 2012/0266872 A1 | 10/2012 | Tanaka et al. |
| 2012/0285447 A1 | 11/2012 | Schipper et al. |
| 2013/0037020 A1 | 2/2013 | Tanaka et al. |
| 2015/0231341 A1 | 8/2015 | Korneff |

FOREIGN PATENT DOCUMENTS

| | | |
|---|---|---|
| EP | 0 711 609 A3 | 7/1995 |
| EP | 0 786 263 B1 | 1/1997 |
| EP | 0 938 906 | 3/1999 |
| EP | 1 439 875 B1 | 10/2002 |
| EP | 1 673 124 B1 | 9/2004 |
| EP | 2 548 599 A1 | 2/2011 |
| WO | WO 92/15354 | 2/1992 |
| WO | WO 2011/135915 A1 | 11/2011 |
| WO | WO 2011/158715 A1 | 12/2011 |
| WO | WO 2011/158716 A1 | 12/2011 |
| WO | WO 2013/013852 A1 | 1/2013 |
| WO | WO 2013/099397 A1 | 7/2013 |
| WO | WO 2013/099398 A1 | 7/2013 |
| WO | WO 2013/099399 A1 | 7/2013 |

OTHER PUBLICATIONS

PCT Written Opinion from PCT/IB2013/002419 dated Mar. 24, 2014.

Extended European Search Report for Application No. EP13852120, mailing date Jun. 22, 2016 (9 pgs).

* cited by examiner

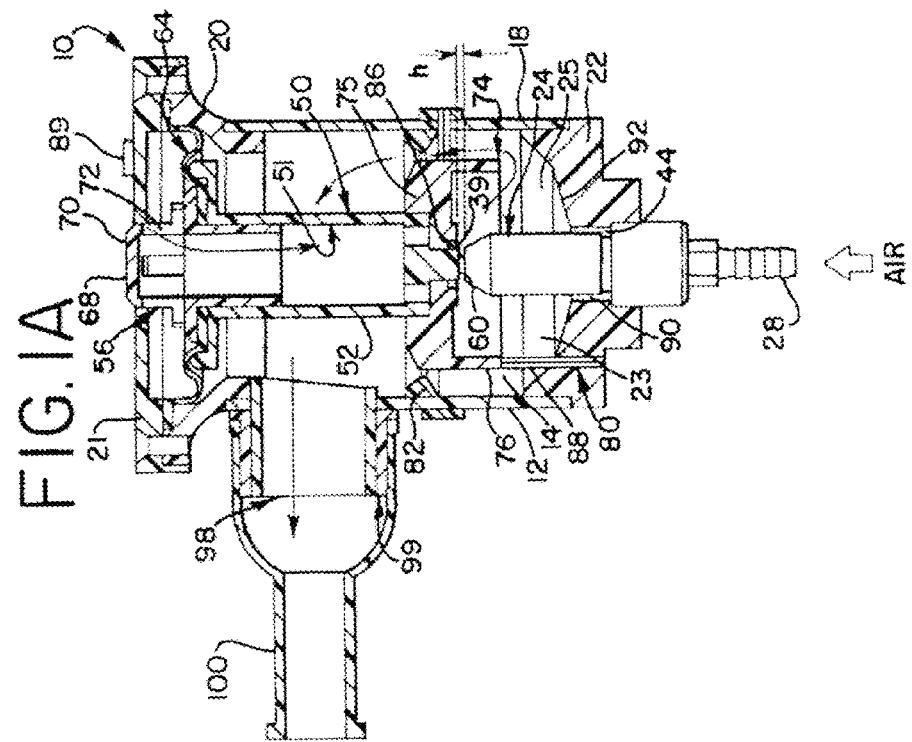
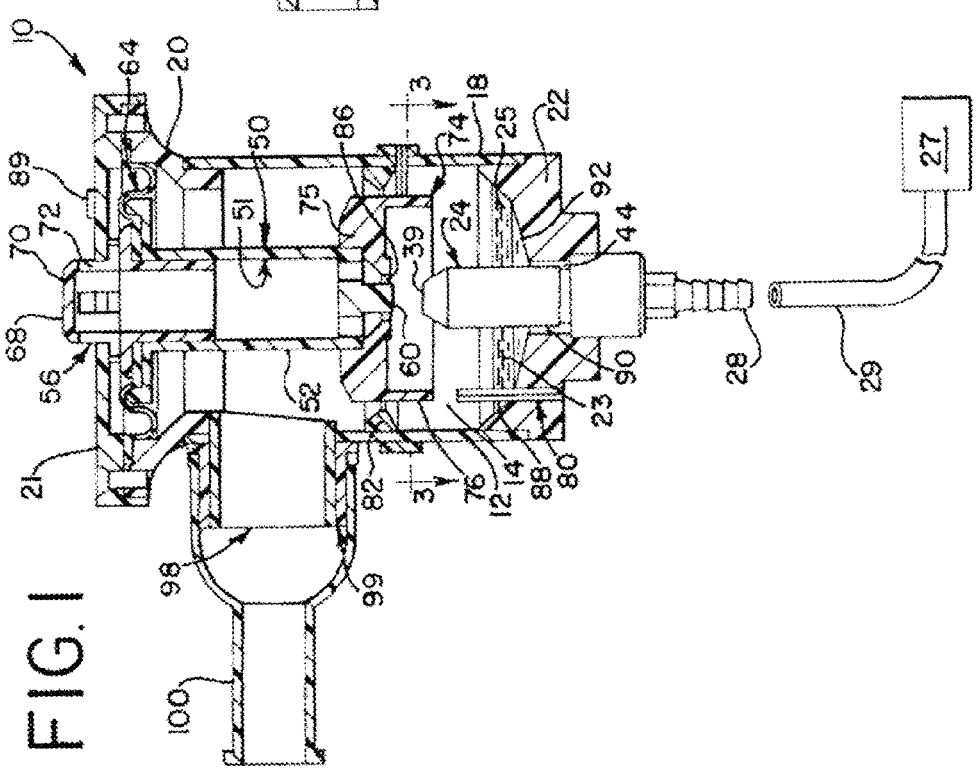

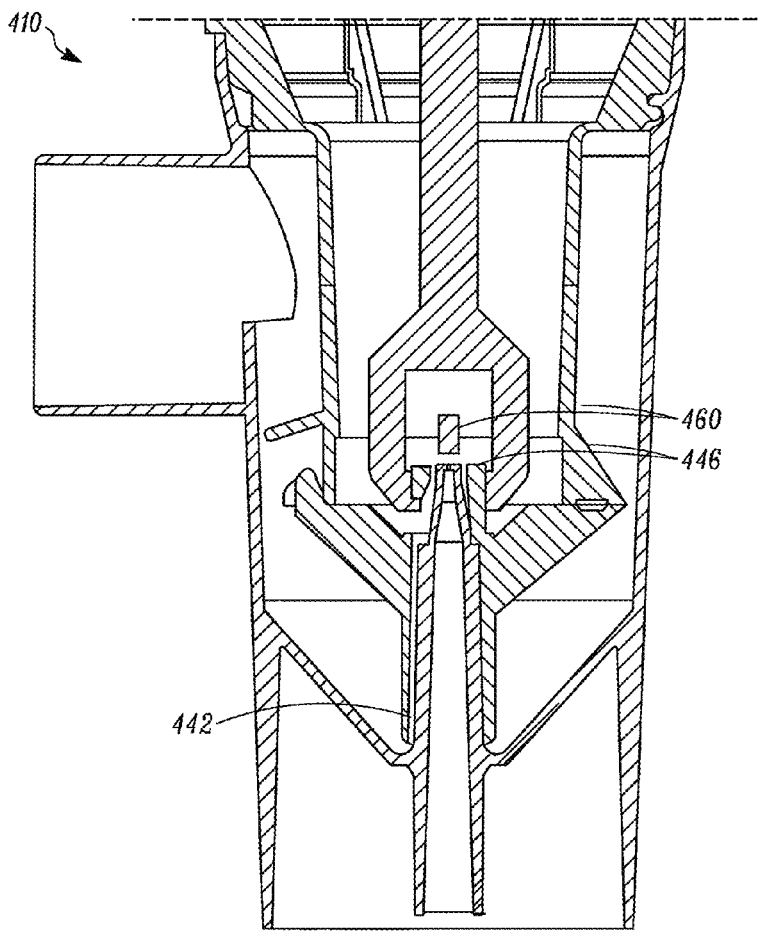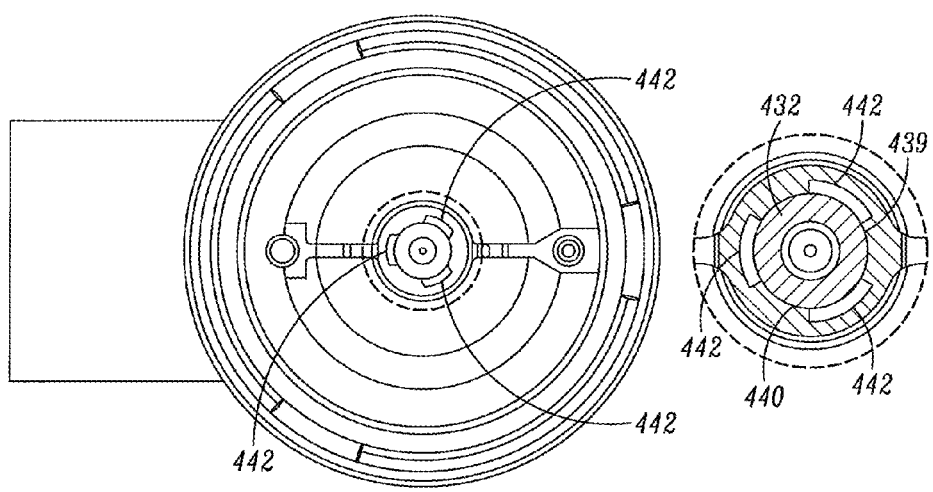
FIG. 8

TWO-MINUTE CONTINOUS DRUG OUTPUT TEST RESULTS
AEROSOL OUTPUT RATE COMPARISON
HIGH OUTPUT BAN DESIGN VS. AEII BAN DESIGN

AEROSOL OUTPUT RATE (μg/min)

AIR SUPPLY PRESSURE (psi)

▨ ϕ1.5mm BAFFLE/ LARGE (PREFERRED) LIQUID CHANNEL SIZE
▨ LARGE BAFFLE/ SMALL LIQUID CHANNEL SIZE

*FIG. 10*

TWO MINUTE CONTINUOUS DRUG OUTPUT TEST RESULTS
EFFECT OF BAFFLE SIZE ON AEROSOL OUTPUT

TOTAL AEROSOL OUTPUT (μg/min)

BAFFLE DIAMETER (mm)

NOTE:
1. DEVICES TESTED FOR 2 MINUTES CONTINUOUS USING 20 PSI WALL AIR SUPPLY PRESSURE

▨ PREFERRED (INCREASED) LIQUID CHANNEL     ▨ AEII LIQUID CHANNEL

*FIG. 11*

EFFECT OF BAFFLE SIZE ON AEROSOL OUTPUT RATE
50% INCREASE IN AEII LIQUID CYLINDER CROSS SECTIONAL AREA

Ø 1.50 MM BAFFLE / 50% INCREASE IN AEII LIQUID CYLINDER CROSS SECTIONAL AREA

Ø 3.5 MM BAFFLE / 50% INCREASE IN AEII LIQUID CYLINDER CROSS SECTIONAL AREA

NOTE:
1. DEVICE TESTED USING 5 LMP AIR SUPPLY
2. DEVICE TESTED WITH DIAL SET TO CONTINUOUS MODE OF DELIVERY

FIG. 12

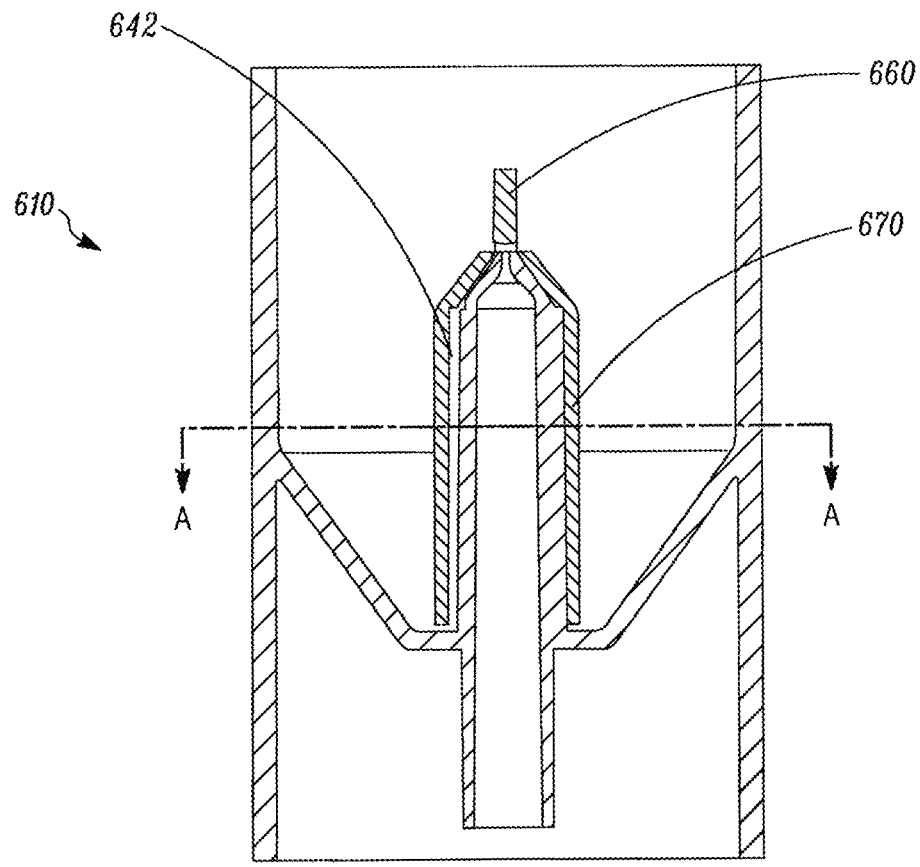
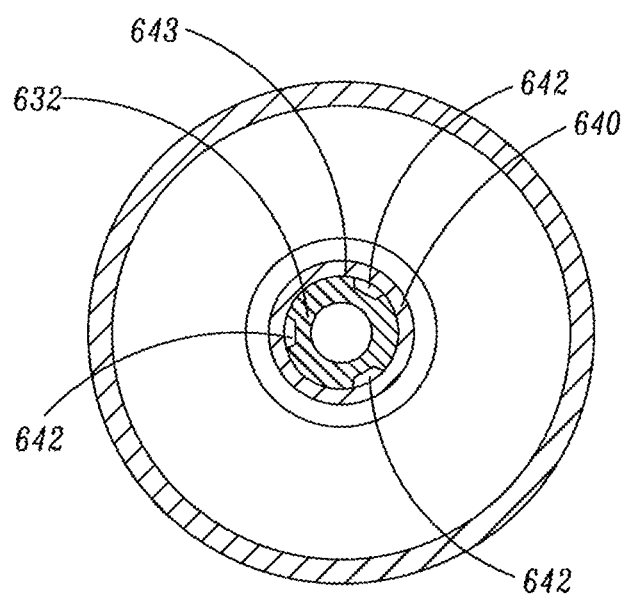
*FIG. 15*

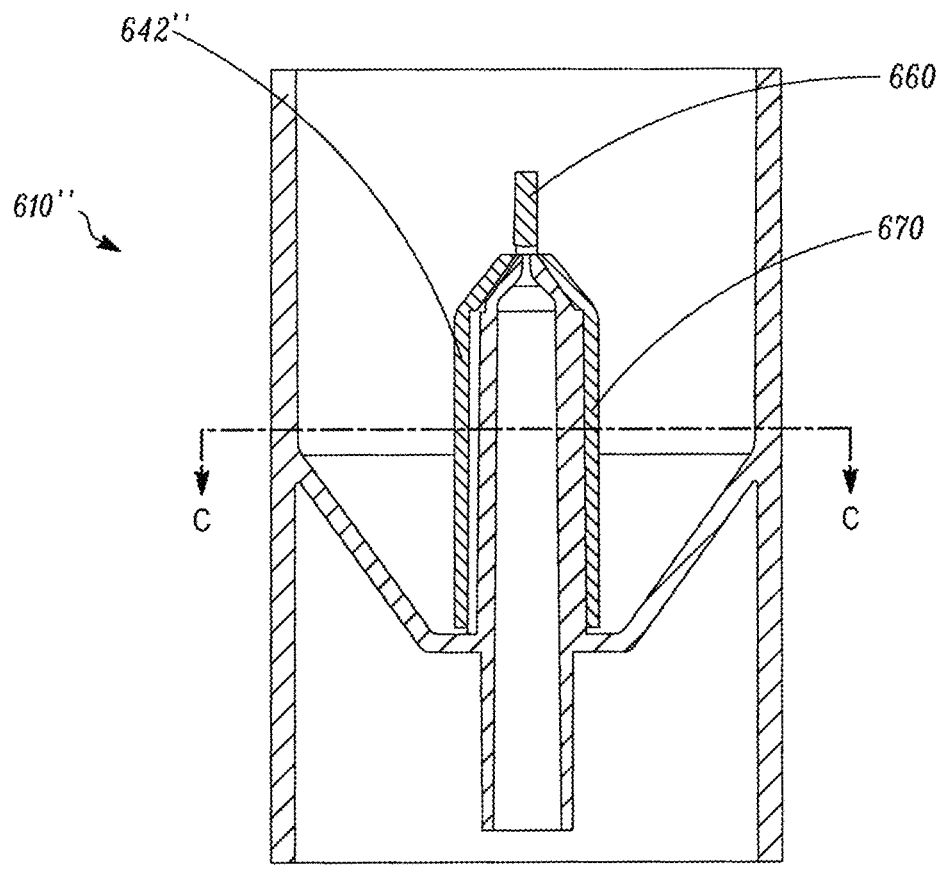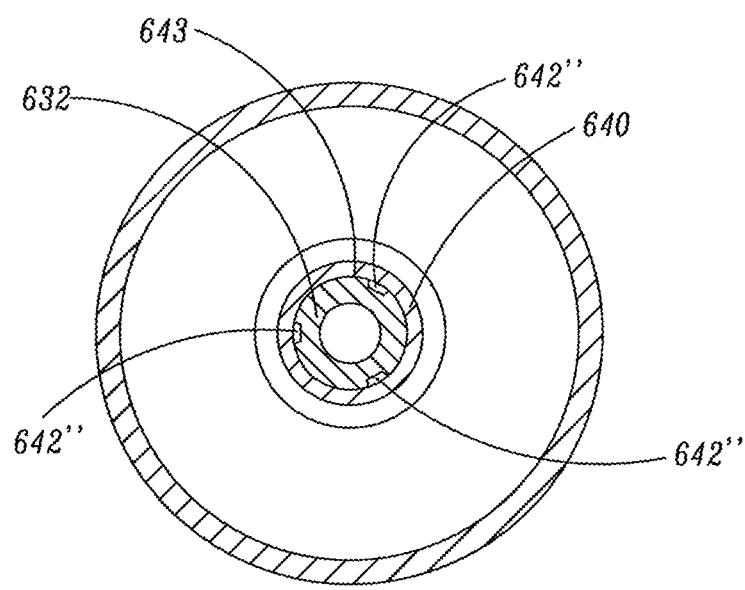
FIG. 17

EFFECT OF LIQUID CHANNEL SIZE ON AEROSOL OUTPUT RATE FOR COMMERCIAL NEBULIZER

CUMULATIVE EMITTED FINE DROPLET MASS UNDER SIMULATED BREATHING CONDITIONS

FIG. 19

NEBULIZER APPARATUS

RELATED APPLICATIONS

This application claims the benefit of U.S. Provisional Application No. 61/720,678, filed on Oct. 31, 2012, which is incorporated herein by reference.

TECHNICAL FIELD

The present invention relates to an apparatus for delivering an aerosol, nebulized liquid, solid medicine, or a vapor to a patient's respiratory tract, and more particularly, to a nebulizer with improved performance.

BACKGROUND

Medical nebulizers for aerosolizing a liquid medicine that can be inhaled by a patient are well known devices commonly used for the treatment of certain conditions and diseases. Nebulizers have applications in treatments for conscious, spontaneously-breathing patients and for controlled ventilated patients.

In some nebulizers, a gas and a liquid are mixed together and directed against a baffle. As a result, the liquid is aerosolized, that is, the liquid is caused to form into small particles that are suspended in the air. This aerosol of the liquid can then be inhaled into a patient's respiratory tract. One way to mix the gas and liquid together in a nebulizer is to pass a quickly moving gas over a liquid orifice tip of a tube. The negative pressure created by the flow of pressurized gas is a factor that contributes to drawing the liquid out of the liquid orifice tip into the stream of gas and nebulize it.

Some of the considerations in the design and operation of nebulizers include regulation of dosages and maintenance of consistent aerosol particle size. In conventional nebulizer design, pressurized gas may entrain a liquid against a baffle on a continuous basis until the liquid in a reservoir is depleted. Continuous nebulization may result in a waste of aerosol during a patient's exhalation or during a delay between a patient's inhalation and exhalation. This effect may also complicate regulation of dosages because the amount of wasted aerosol may be difficult to quantify. Also, continuous nebulization may affect particle size and/or density. In addition, there may be excess medication lost to condensation on the nebulizer or mouthpiece during periods of non-inhalation. On the other hand, interrupted nebulization may also affect particle size and density as the nebulization is turned on and off.

There are several other considerations that relate to the effectiveness of nebulizer therapies. For example, it has been suggested that nebulization therapy is more effective when the generation of aerosol particles is relatively uniform, for example, producing particles of a particular size, particles within a range of sizes, and/or particles a substantial percentage of which are within a range of sizes. In addition, it may be advantageous for a nebulizer to be able to generate a large amount of aerosol quickly and uniformly so that a proper dosage can be administered.

A further consideration is the environment in which the nebulizer therapy may be administered. For example, a wall outlet at a hospital may supply pressurized gas for use with a nebulizer at a flow rate of 4 to 10 liters per minute in a range from 45 psi to 55 psi, whereas a home care compressor may supply pressurized gas for use with a nebulizer at a flow rate of 3-5 liters per minute and at pressures of 15 to 30 psi.

Regardless of the environment in which the nebulizer therapy is administered, it is desirable to maintain and/or improve performance of nebulizers.

Additional considerations in the design and operation of nebulizers relate to the size and shape of the baffle, and the volume of liquid available for nebulization contained between the reservoir and the liquid orifice.

Accordingly, with these considerations taken into account, there is a need for an improved nebulizer.

BRIEF SUMMARY

The present disclosure provides an apparatus for delivering nebulized liquid or solid medication or vapor to a patient. According to one aspect, a nebulizer includes a housing having a chamber for holding an aerosol, an air outlet communicating with the chamber for permitting the aerosol to be withdrawn from the chamber, and a reservoir for holding a liquid to be aerosolized. The nebulizer also includes a liquid orifice located in the chamber, one or more liquid channels defined between the reservoir and the liquid orifice, the one or more liquid channels having a liquid volume, and a pressurized gas outlet located in the chamber adjacent to the liquid orifice. A baffle is located in the chamber and positioned relative to the pressurized gas outlet and the liquid outlet so as to divert pressurized gas from the pressurized gas outlet and over the liquid orifice. The baffle has a diverter surface area.

In another aspect, the liquid volume is at least 80 $mm^3$.

In another aspect, the diverter surface area is less than 5.0 $mm^2$.

In another aspect, the liquid volume is less than 1000 $mm^3$.

In another aspect, the diverter surface area is greater than 0.75 $mm^2$.

In yet another aspect the liquid volume is between 250 $mm^3$ and 300 $mm^3$.

In yet another aspect the diverter surface area is between 1.5 $mm^2$ and 2.0 $mm^2$.

In a further aspect, the baffle has a disc-shaped diverter surface area. The disc-shaped diverter surface area may have a diameter between 1.0 mm and 2.5 mm.

In a further aspect, the baffle is shaped as a rib.

In another aspect, the baffle has a diverter surface area at least 50% of a cross-sectional area of the liquid orifice.

In a different aspect, the liquid orifice is positioned at a distal end of a first nozzle extending in to the chamber, and the pressurized gas outlet is positioned at a distal end of a second nozzle extending in to the chamber through the first nozzle. The one or more liquid channels may be formed between the first nozzle and the second nozzle.

BRIEF DESCRIPTION OF THE DRAWINGS

FIG. 1 is a partial cross-sectional side view of a first embodiment of a nebulizer;

FIG. 1A is a cross-sectional view of the nebulizer of FIG. 1 shown in an inspiration cycle;

FIG. 8 is a cross-sectional side view of a fourth embodiment of a nebulizer with particular dimensions intended to improve performance of the nebulizer;

FIG. 10 is a graph comparing aerosol output rates for tests performed on modified versions of the nebulizer of FIG. 4;

FIG. 11 is graph comparing aerosol output rates for additional tests performed on modified versions of the nebulizer of FIG. 4;

FIG. 12 is a graph comparing aerosol output rates for tests performed on modified versions of the nebulizer of FIG. 4;

FIG. 15 is a cross-sectional side view of a sixth embodiment of a nebulizer;

FIG. 17 is another cross-sectional side view of the nebulizer of FIG. 15 with particular dimensions modified to alter the performance of the nebulizer;

DETAILED DESCRIPTION

Figure 2:
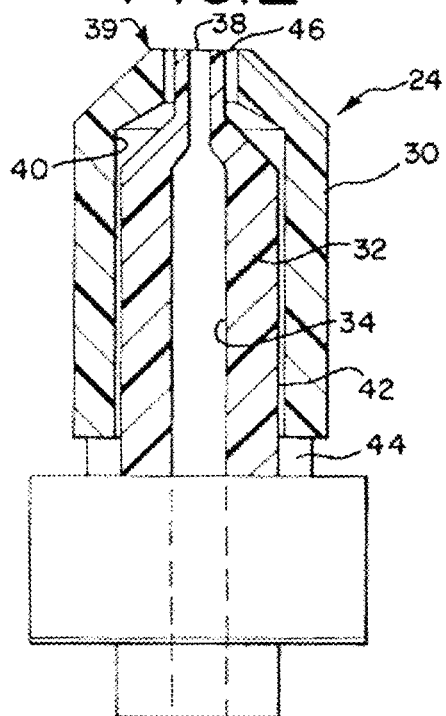
FIG. 2 is a cross-sectional view of the nozzle assembly of the nebulizer of FIG. 1.

A nebulizer 10 is illustrated in FIG. 1. The nebulizer 10 is a small volume nebulizer and includes a housing or container 12 defining an internal chamber 14. The housing 12 is formed of a cylindrically-shaped side wall portion 18, a top portion 20, and a bottom portion 22. The component parts of the housing 12 may be formed of separate, multiple pieces of material that are connected together by welding, adhesives, etc., or more preferably, some of the component parts may be formed together of a single piece of material formed by an injection molding process. For example, the bottom, and side portions 22 and 18 may be formed of separate pieces that are connected together, or preferably, these parts may be formed of one piece of molded plastic. Any of a number of plastics may be suitable, including polycarbonate, or polycarbonate blends. A cover 21 is removably mounted on the upper portion of the housing 12, such as by means of a snap-on cover arrangement, twist-lock threads, screws or other types of fasteners. The housing 12 is approximately 6 cm in height and has a diameter of approximately 4 cm.

Figure 3:
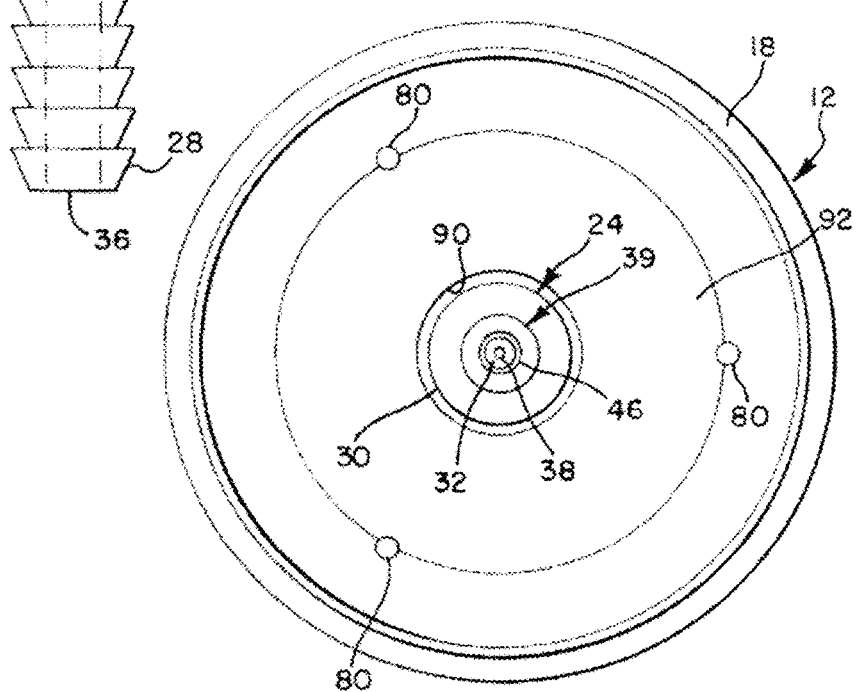
FIG. 3 is a cross-sectional top view of the nebulizer of FIG. 1 taken along line 3-3' (without the cover for clarity)

A lower portion 23 of the chamber 14 serves as a reservoir for holding a fluid 25 for nebulizing, such as a solution containing a medication. Located in the lower portion 23 of the housing 12 is a nozzle assembly 24. Referring to FIGS. 1-3, the nozzle assembly 24 extends downward from the chamber 14 of the housing 12 to a fitting 28 located external of the chamber 14 on a bottom side 22 of the housing 12. The fitting 28 is sized to connect to a supply 27 of pressurized gas provided through conventional tubing 29. The pressurized gas may be supplied by any suitable source, such as a conventional gas supply used in hospitals, a pump, compressor, cartridge, canister, etc.

The nozzle assembly 24 is comprised of an outer tubular member 30, and an inner tubular member 32. The outer tubular member 30 has an inner passageway 40 that defines a liquid cylinder. The inner passageway 40 has a cross-sectional shape that is generally circular along the length of the inner passageway 40. The inner tubular member 32, or gas nozzle, has a passageway 34 that extends from an opening 36 in the bottom end of the fitting 28 to a gas outlet orifice 38 located at a top end 39 of the nozzle assembly 24. The inner tubular member 32 is located in the inner passageway 40 of the outer tubular member 30. The inner tubular member 32 is sized to slide into the inner passageway 40 of the outer tubular member 30 so that it is aligned therein. One or more liquid channels 42 are formed between the outer tubular member 30 and the inner tubular member 32. The one or more liquid channels 42 may comprise an annular gap between the outer tubular member 30 and the inner tubular member 32, and/or any cut-outs, passageways, slots, etc. formed between the inner tubular member 32 and the outer tubular member 30, whether on the outer surface of the inner tubular member 32 (e.g., as one or more slots), on the inner surface of the outer tubular member 30 (e.g., as one or more slots), or any combination thereof (e.g., as an annular gap and slots). The one or more liquid channels 42 extend from a liquid reservoir opening 44 located at the reservoir 23 of the lower portion of the chamber 14 to a liquid outlet orifice 46 located at the top end 39 of the nozzle assembly 24. The one or more liquid channels 42 serve to convey liquid medicine from the reservoir 23 at the bottom of the chamber 14 to the liquid outlet orifice 46 at the top of the nozzle assembly 24. The one or more liquid channels 42 has a liquid volume or an equivalent liquid volume defined by the aggregate volume between the outer tubular member 30 and the inner tubular member 32 (including any gaps, passageways, or slots) extending from the reservoir opening 44 to the liquid outlet orifice 46. As explained below, dimensions of the components defining the liquid volume may be selected to alter the performance of the nebulizer. In alternative embodiments, such as those shown and described herein, the outer tubular member 30 and the inner tubular member 32, or portions thereof, may have other than a cylindrical shape, such as for example, a conical shape.

As shown in FIG. 3, the liquid outlet orifice 46 is located at a top end of the liquid cylinder, or inner passageway 40 of the outer tubular member 30. The liquid outlet orifice 46 has an annular shape defined by the top ends of the outer tubular member 30 and the inner tubular member 32 of the nozzle assembly 24. The gas outlet orifice 38 has a circular shape and is located concentrically of the annular liquid orifice. In the present embodiment, the gas outlet orifice 38 is approximately 0.56 mm diameter and the liquid outlet orifice 46 has an outer diameter of approximately 2.79 mm to 3.18 mm and an inner diameter of approximately 2.13 mm. These dimensions are provided only by way of example and the nebulizer may be made in other sizes with different dimensions, as explained herein, in order to alter the performance of the nebulizer.

The top end 39 of the nozzle assembly 24 is formed by the top ends of the outer and inner tubular members 30 and 32. In the present embodiment, the top end 39 is a generally flat surface having a diameter of approximately 4.57 mm. In alternative embodiments, the top end 39 may have an other-than-flat shape, for example, the inner tubular member 32 may be spaced above the outer tubular member 30 so that the liquid orifice 46 is located below the gas orifice 38. Likewise, the diameter may be larger or smaller.

The nozzle assembly 24, or a portion thereof, may be formed as part of the housing 12 as a single piece of material in an injection molding process. For example, the inner tubular member 32 may be formed of the same piece of injected molded plastic as the bottom of the housing 12.

Referring again to FIG. 1, the nebulizer 10 also includes a chimney assembly 50. The chimney assembly 50 is located in an upper portion of the chamber 14 above the liquid reservoir 23. The chimney assembly 50 includes a tubular body 51 that defines an internal passageway 52 that extends from an inlet opening 56 in the housing cover 21 to a chimney outlet opening at a bottom end of the tubular body 51. Thus, the chimney assembly 50 serves as an inlet channel for ambient air to enter into the chamber 14. The inlet opening 56 communicates with ambient air (through ports of an actuator button, as described below) and the chimney outlet opening communicates with the chamber 14.

Located on the lower end of the chimney assembly 50 is a baffle 60. The baffle 60 may be formed of the same piece of molded plastic material as the chimney 50 or alternatively, the baffle 60 may be formed of a separate piece of material that is attached by suitable means to the rest of the chimney assembly 50. The baffle 60 is located directly opposite from the gas outlet orifice 38 and the liquid outlet orifice 46 located at the top end 39 of the nozzle assembly 24. The baffle 60 is movable so that the distance between the baffle 60 and the top surface 39 of the nozzle assembly 24 can be varied. In the present embodiment, the baffle 60 has of a flat circular or disc shape with a diameter of approximately 4.57 mm so that it extends over both the gas and liquid orifices 38 and 46 out to approximately the edge of the top surface 39 of the nozzle assembly 24. The baffle 60 therefore has a disc-shaped diverter surface area of approximately 16.40 mm$^2$. As used herein, diverter surface area refers to the surface area (whether flat, angled, or curved) of the baffle located opposite from the gas outlet orifice 38 and the liquid outlet orifice 46 that is provided for obstructing the flow of air and gas exiting the liquid outlet orifice and the gas outlet orifice. As explained below, the dimensions of the baffle disc may be selected to alter the performance of the nebulizer. In alternative embodiments, the baffle 60 may have an other-than circular shape such as, for example, a rib, or a cone, or a hemispherical shape. It is preferable that the baffle 60 have a size and shape such that the baffle 60 has a diverter surface area at least 50% of the liquid outlet orifice 46. In another embodiment the baffle and nozzle assembly remain fixed and are not movable such that the distance between the diverter surface of the baffle 60 and the top surface 39 of the nozzle assembly 24 cannot be varied. In yet another embodiment the baffle remains fixed and is not movable, but the nozzle assembly, or a portion thereof, is movable such that the distance between at least a portion of the nozzle assembly and the diverter surface of the baffle 60 can be varied.

The chimney assembly 50 is connected to the housing 12. Specifically, the chimney assembly 50 is attached to the top portion 20 of the housing 12 by means of a membrane or diaphragm 64. The membrane 64 is a ring-shaped piece of a flexible, resilient material, such as silicone rubber. An outer rim or bead of the membrane 64 is secured in a groove in the top portion 20 of the housing 12 and/or the cover 21. An inner rim of the membrane 64 is secured in a slot formed by two parts of the chimney assembly 50. The membrane 64 has a rolled cross-sectional profile as shown in FIG. 1. This permits the membrane 64 to act as a rolling diaphragm. The membrane 64 permits limited movement of the chimney assembly 50. The chimney assembly 50 is connected to the membrane 64 so that the membrane 64 biases the chimney assembly 50 away from the nozzle assembly 24 as shown in FIG. 1. When installed in the manner shown in FIG. 1, in the present embodiment, the bottom of the chimney assembly 50 is approximately 3.81 mm away from the top surface of the nozzle assembly 24. In alternative embodiments, the bottom of the chimney assembly 50 may be closer or farther away from the top surface of the nozzle assembly 24.

Located at the top end of the chimney assembly 50 is an actuator 68. The actuator 68 connects to the tubular body 51 of the chimney assembly 50 and extends through the opening 56 at the top of the housing 12 in the cover 21. The actuator 68 includes a closed top side 70 with one or more side opening ports 72.

Located in the chamber 14 at the bottom end of the chimney assembly 50 is a bell-shaped cover 74. The cover 74 extends from the opening at the bottom of the chimney passageway 51 outward toward the inside wall of the cylindrical portion 18 of the housing 12. The cover 74 includes a horizontal portion 75 and a vertical portion 76 that extends downward from the horizontal portion 75 toward the top of the nozzle assembly 24. The cover 74 has an open bottom side providing an air passageway around the bottom side of the cylindrical vertical wall 76.

As mentioned above, the baffle 60 is movable relative to the nozzle assembly 24. The present embodiment provides a means to limit the travel of the baffle relative to the nozzle assembly 24. This may be accomplished in any of several suitable ways. In a present embodiment, the movement of the baffle 60 toward the nozzle assembly 24 is limited by one or more stop pins 80. The stop pins 80 extend up from the bottom portion 22 of the housing. In a present embodiment, there are three stop pins. The top ends of the stop pins 80 are spaced away from the bottom end of the vertical wall 76 of the cover 74. Because the chimney assembly 50 is movable vertically due to its connection to the housing 12 by means of the flexible membrane 64, the stop pins 80 provide a lower limit to the movement of the chimney assembly 50. In a present embodiment, the stop pins 80 are spaced so that when the lower edge of the vertical wall 76 of the cover 74 is brought into contact with the stop pins 80, a space 'h' is provided between the baffle 60 and the upper surface 39 of the nozzle assembly 24. In the present embodiment, the space 'h' is approximately between 0.64 mm and 1.14 mm, or more preferably approximately between 0.76 mm and 1.02 mm, and most preferably approximately 0.84 mm. In alternative embodiments, the space 'h' may be larger or smaller.

In alternative embodiments, movement of the baffle 60 toward the nozzle assembly 24 may be limited by means other than stop pins. For example, if the housing were formed by an injection molding process, steps, shoulders, fins, or other structures, may be provided along the walls of the housing in order to limit the downward travel of the chimney and/or baffle.

Also located in the chamber 14 is a diverting ring 82. The diverting ring 82 is located on the inner wall of the cylindrical portion 18 of the housing 12. Specifically, the diverting ring 82 is positioned adjacent to the cover 74. The diverting ring 82 is sized to define a gap 86 around the cover 74. The diverting ring 82 serves to impede large droplets of liquid that might form on the inner wall of the housing 12 and divert large droplets back down into the reservoir 23 at the bottom of the housing 12. In addition, the diverting ring 82 serves to provide a relatively tortuous path for the flow of aerosol particles from the lower portion of the chamber 14 to the upper portion. This tortuous path also serves to reduce the presence of larger particles and helps to make the particle size distribution more uniform.

As mentioned above, the bottom of the chamber 14 serves as a reservoir 23 for a liquid to be nebulized. In a present embodiment, the reservoir has a funnel-like shape to direct the liquid to be nebulized in a downward direction toward the inlet 44. The reservoir portion of the chamber 14 is formed of at least two portions or stages. In a present embodiment, an upper portion 88 of the reservoir is relatively wide having a diameter approximately the same as that of the cylindrical portion 18 of the housing 12 (e.g. 6 cm). The upper portion 88 is relatively shallow (e.g. 7.94-6.35 mm). The upper portion 88 of the reservoir tapers in a funnel-like manner toward a lower portion 90 (or secondary well) of the reservoir. The lower portion 90 is relatively narrow, but relatively deep (e.g. 6.35 mm). The lower portion 90 of the reservoir is slightly wider (e.g. 15.88 mm) than the outer diameter of the nozzle assembly 24. The opening 44 from which the liquid is drawn is located at the bottom of the lower portion 90 of the reservoir. In a present embodiment, the reservoir 23 also includes an intermediate portion 92 located between the upper portion 88 and the lower portion 90. The intermediate portion 92 of the reservoir 23 has a height and a width between that of the upper and lower portions.

In the embodiment of the nebulizer shown in FIG. 1, the relative sizes and dimensions of the upper, lower and intermediate portions of the reservoir 23 contribute to the generation of an aerosol wherein the aerosol particle size and output is relatively uniform overall. As described more below, the liquid in the reservoir 23 is drawn through the opening 44 and up the liquid channel 42 in part by the negative pressure caused by the flow of gas across the liquid orifice 46. The suction force provided by the gas flow both draws the liquid up out of the reservoir to the top of the nozzle and entrains the liquid with a certain velocity in the air flow. As the liquid is nebulized, the surface level of the liquid in the reservoir goes down, thereby directly increasing the distance that the liquid has to be drawn up out of the reservoir to the orifice at the top of the nozzle. As the distance of the top of the nozzle over the liquid surface increases, more energy is required to draw the liquid up to the liquid orifice at the top of the nozzle assembly 24. Assuming a relatively constant gas pressure, this increasing distance may have the effect of decreasing liquid flow through the liquid orifice which in turn may affect the uniformity of the aerosol particle size and rate.

The embodiment of the nebulizer in FIG. 1 reduces this possible adverse effect. With the embodiment of FIG. 1, a relatively large portion of the liquid is stored in the upper portion 88 of the reservoir and a relatively smaller portion of the liquid is stored in the lower portion 90 of the reservoir. Since the large portion 88 of the reservoir is wide and relatively shallow, the surface level of the liquid in the reservoir changes relatively slightly as the liquid in this portion of the reservoir is drawn down. Therefore, there is little change in the energy needed to draw this amount of liquid up from the reservoir to the liquid orifice 46 as this portion of the liquid is depleted. When all the liquid in the upper portion 88 of the reservoir is nebulized, the remaining liquid in the lower portion 90 of the reservoir is drawn into the liquid channel 42 and the height of the top surface of the liquid falls rapidly. However, since the lower portion 90 of the reservoir is relatively narrow, it contains only a small portion of the liquid being nebulized so there is relatively little overall effect on aerosol particle size and output from this portion of the liquid.

The embodiment of the nebulizer shown in FIGS. 1-3 is adapted for use by a spontaneously breathing patient, so the aerosol from the nebulizer is output to a mouthpiece or mask that can be used by the spontaneously breathing patient. Accordingly, located in an upper portion of the chamber 14 is an adapter 99 having a chamber outlet 98 that connects to a mouthpiece 100. In alternative embodiments, the nebulizer may be used with ventilator systems and instead of the mouthpiece 100, the adapter 99 would connect the outlet 98 to the ventilator circuit.

To operate the nebulizer 10, a suitable amount of a liquid such as a medicine or water is placed in the reservoir of the chamber 14. The liquid may be placed in the reservoir by first removing the cover 21, membrane 64, and chimney 50, filling an appropriate amount of liquid into the reservoir, and replacing the cover 21, membrane 64, and chimney 50 onto the housing 12. In a preferred embodiment, the cover, membrane and chimney are assembled together and would be removable together as a unit. Alternatively, the liquid may be placed into the reservoir through the mouthpiece 100, or further, the nebulizer may be provided pre-filled with the appropriate amount of medicine from the manufacturer, or in yet another alternative, the nebulizer may be provided with a resealable fill port. The source of pressurized gas 27 is connected to the fitting 28. The source of pressurized gas 27 may be an external source, for example, a hospital wall outlet that provides pressurized gas at a flow rate of 4 to 10 liters per minute in a range from 45 to 55 psi, or a home care compressor that provides gas a flow rate of 3 to 5 liters per minute and in a range of 15 to 20 psi. Gas is delivered through the passageway 34 and is expelled from the gas outlet orifice 38 into the chamber 14. However, at this stage, prior to inhalation by the patient, the gas travels upward from the gas outlet orifice 38 and nebulization does not occur since the baffle 60 is in the non-nebulizing position. The membrane 64 holds the chimney assembly 50, including the baffle 60, away from the nozzle 24. In one embodiment, when in the non-nebulizing position, the distance between the baffle 60 and the top of the nozzle is approximately 3.81 mm. At this distance, the gap between the baffle 60 and the nozzle 24 is such that the flow of gas does not create sufficient negative pressure over the liquid orifice 46 to draw out the liquid.

To generate an aerosol with the nebulizer, the patient places the mouthpiece 100 to his/her mouth. When the patient inhales, air is withdrawn from the chamber 14 reducing the pressure inside the housing 12. The lower pressure in the chamber 14 causes the membrane 64 to flex drawing the chimney 50 down. The lower position of the chimney 50 is shown in FIG. 1A. Downward movement of the chimney 50 is limited by the stop pins 80. When the stop pins 80 limit the downward movement of the chimney 50, the baffle 60 its diverter surface area are spaced a predetermined distance 'h' from the top surface 39 of the nozzle assembly 24. In one embodiment, the gap 'h' is approximately 0.84 mm. In alternative embodiments, the distance 'h' may be larger or smaller, as described herein, in order to alter the performance of the nebulizer.

The pressurized gas, which may be continuously injected into the nebulizer through the fitting 38, is diverted sideways approximately 90 degrees by the baffle 60. Since the gas outlet orifice 38, baffle 60 and nozzle top 39 are generally circular, gas exiting the orifice 38 is dispersed evenly in an approximately 360 degrees or radial pattern. The liquid medicine in the reservoir is then drawn up the channel 42 and out of the liquid outlet orifice 46 in part by the negative pressure caused by the moving gas passing over the liquid outlet orifice. The liquid drawn into the diverted gas stream is aerosolized at least by the time it reaches the larger volume space of the chamber. In one embodiment, the liquid medicine drawn out of the liquid orifice 46 has little or no impaction against the baffle 60. However, in alternative embodiments, the liquid drawn into the gas stream may be directed against the baffle 60.

As the liquid is nebulized it travels into the chamber 14 along a path around the lower edge of the cover 74. As the patient inhales, the nebulized liquid travels upward through the gap 86 between the cover 74 and the diverting ring 82, and out through the mouthpiece 100 to the patient's respiratory tract.

When the patient ceases to inhale, the pressure in the chamber 14 rises. The biasing of the membrane 64 is again sufficient to move the chimney 50 upward, increasing the distance between the baffle 60 and the top surface 39 of the nozzle assembly 24, and causing nebulization of the liquid to cease. In alternative embodiments, a spring, pneumatic valve, or other biasing device may be utilized, alone or in combination with each other and the membrane, to move the baffle 60 into a non-nebulizing position. Thus, the nebulizer automatically cycles aerosol generation in time with the breathing cycle of the patient.

If the patient exhales into the nebulizer, no nebulization occurs since the baffle 60 is in the non-nebulizing position due to the biasing of the membrane 64. Upward travel of the chimney 50 is limited by the cover 21.

During inhalation, some air flow may be provided through the nebulizer in a path through the chimney 50. This air flow into the chamber 14 may be provided from ambient in a path provided through the ports 72, the chimney inlet 56, the chimney passageway 52, and the chimney outlet. This air flow may continue during both inhalation when the chimney 50 is in the lower position and exhalation when the chimney is in the higher position. Alternatively, the air flow through the chimney 50 may be stopped or reduced during inhalation when the chimney 50 is in the lower position. Control of the airflow through the nebulizer during inhalation or exhalation may be effected by suitable selections of the dimensions of the chimney inlet 56, the chimney outlet, the actuator ports 72, the baffle ring 82, and other components that affect airflow through the chamber, such as any filters.

In the embodiment described above, the membrane 64 provides an elastic triggering threshold that permits cyclical nebulization to occur that coincides with the breathing of the patient. This threshold is set to fall within normal human breathing parameters so that the baffle moves into and out of proximity with the nozzle top as a result of the patient's normal breathing. In one embodiment, this level may be approximately less than or equal to 3.0 cm of water.

It can be appreciated that the threshold may be established at different levels to account for different classes of patients. For example, if the nebulizer is designed to be used with infants or neonatals, the elastic threshold of the membrane may be lower than the threshold used for adults. Similarly, a different threshold may be used for geriatric patients. The nebulizer may be used also for veterinary applications, such as equine or canine. In veterinary applications, there may be a relatively wide range of thresholds related to the various sizes of animals. Nebulizers having suitably chosen operating thresholds can be designed for veterinary uses.

It is also recognized that the openings into the chamber, such as the opening 56, may affect the operating threshold for nebulization. Thus, the operating threshold of the nebulizer may be made readily adjustable by making the actuator 68 adjustable. Alternatively, the operating threshold may be adjusted by selection of the size of the openings 56 and 72 into the chamber which would also control air entrainment. This would permit the user to adjust the thresholds, if desired. By appropriate adjustment of the operating thresholds, flow control through the nebulizer can be provided. For example, it may be desirable that the patient not inhale or exhale too quickly or too deeply. For adults, a suitable flow rate may be approximately 30-60 liters/minute. The openings into and out of the chamber may be suitably adjusted to provide for these rates.

The nebulizer may be operated manually instead of relying on the breath-actuated feature. To operate the nebulizer manually, the actuator 70 is pressed down toward the cover 21. As mentioned above, the actuator 70 is connected to the chimney 50. Pressing the actuator 70 brings the baffle 60 down into the nebulizing position close to the nozzle 24. Release of the actuator 70 causes the chimney 50 to rise due to the biasing of the membrane 64 thereby causing nebulization to cease.

The breath actuation of the nebulizer is convenient and efficient. By cycling the nebulization of the liquid, the nebulizer can be more efficient thereby reducing the cost of the therapy.

An important advantage follows from the feature of this nebulizer that nebulization can be cycled so as to occur in coordination with a physiological cycle of the patient. Specifically, by nebulizing only during an inhalation, for example, the dosage of medication delivered to the patient can be more accurately delivered and monitored. This enables this embodiment of the nebulizer to provide for dosimetric medication delivery to an extent that has been otherwise unavailable. By limiting the medication delivery to the inhalation cycle of the patient, a dosimetric portion of the medication can be provided.

In addition, the nebulizer 10 provides for high output and uniform nebulization due to the arrangement of the gas and liquid orifices 38 and 46 relative to the baffle 60. The annular configuration of the liquid orifice 46 relative to the gas orifice provides for aerosol generation in an approximately 360 degree direction. This enables a relatively high and uniform rate of nebulization.

In a present embodiment, the membrane 64 is biased to keep the chimney in an upper, non-nebulizing position except during inhalation. Thus, in the periods of time between inhalations and exhalations, or if the patient pauses and removes the mouthpiece, nebulizing does not take place. In alternative embodiments, the membrane 64 may bias the chimney downward so that the nebulizer generates an aerosol or nebula except during exhalation. This alternative may not be as efficient as the prior alternative, but may still provide significant advantages over nebulizers that generate aerosol continuously.

In further alternative embodiments of the nebulizer, the gas orifice 38, the gas passageway 34, or a portion thereof, may have a shape that modifies the force of the pressurized gas against the baffle 60. For example, the gas orifice 38 may have a shape that facilitates the change of direction of the gas when it is directed against the baffle, so that the force of the gas would not move the baffle away during inhalation thereby helping to direct the gas out into the chamber. In other embodiments, the geometry may be varied to tailor gas force and flow.

As mentioned above, the membrane 62 serves as a biasing member that moves the baffle. Preferably, the membrane is constructed of a silicone rubber material. Other materials capable of repetitive flexing, compression or expansion in response to the force of inhaled or exhaled air, such as a spring, or elastic bellows, may also be used. The biasing member is constructed so that it will move the baffle a predetermined distance away from or toward the nozzle during the course of a patient's spontaneous or ventilated breathing.

In a present embodiment, the baffle moves up and down in response to the patient's breathing. Alternative embodiments contemplate various means of bringing or diverting the gas and liquid streams into proximity in a cyclical basis.

In alternative embodiments, for instance, instead of moving a baffle into proximity with a gas outlet, the liquid jet or orifice can be moved toward the gas jet or orifice, or is otherwise directed toward the gas jet or orifice, or vice versa. For example, as shown and described in U.S. Pat. No. 6,929,003 (the entirety of which is herein incorporated by reference), particularly with reference to FIGS. 12 and 13 in U.S. Pat. No. 6,929,003, a nozzle cover consists of two portions. A first portion is fixed at the top of a gas nozzle, so that the pressurized gas outlet, baffle, and annular orifice of a fluid outlet are all fixedly positioned with respect to one another at a spacing suitable for nebulization. The second portion is attached to an actuator piston and is moveable a predetermined distance up and down the axis of the gas nozzle so that the annular orifice of the fluid inlet moves with the actuator piston. As with the previously described embodiments, one or more fluid pathways are defined by spacing between the gas nozzle and nozzle cover, grooves in the nozzle cover, grooves in the gas nozzle, or a combination of these options. In the non-actuating position, the second portion is separate from the first portion such that a gap of a predetermined distance exists between the two portions. As a result of the gap, the first portion of the nozzle cover does not contact the fluid reservoir and there is no continuous fluid pathway between the fluid orifices, in other words no pathway exists from the reservoir and fluid inlet to the fluid outlet, so that no fluid may reach the fluid outlet. In the actuating position, the second portion is moved up until it mates or abuts with the first portion. The two portions cooperate to form at least one continuous fluid pathway between the fluid outlet and the reservoir. The continuous fluid pathway permits the negative pressure over the fluid outlet to draw fluid from the reservoir and initiate nebulization.

In alternative embodiments, the entire nozzle 24 can move instead of the baffle, or alternatively, both the nozzle and the baffle can move. Also, in a present embodiment, the baffle movement is up and down, but in alternative embodiments, the movement can be side to side, rotating, or pivoting. Finally, in other embodiments, the baffle, orifices, nozzle, and other elements may all be fixed so that the nebulizer is a continuous nebulizer rather than a breath-actuated nebulizer.

In alternative embodiments of the nebulizer, the liquid orifice may have shapes other than annular. For example, the liquid orifice may be located aside the gas orifice. Alternatively, the liquid orifice may be formed of a series of orifices positioned aside or annularly around the gas orifice.

Further descriptions of some of the previously described nebulizers may be found in U.S. Pat. Nos. 5,823,179; 6,044,841; and, 6,929,003, the entireties of which are herein incorporated by reference. The concepts described herein may be applied to the foregoing U.S. patents and to other nebulizers as described in U.S. Pat. Nos. 6,450,163; 7,270,123; 7,634,995; 7,905,228; and 8,397,712 (the entireties of which are herein incorporated by reference), as well as to commercially available nebulizers, including for example, the AEROECLIPSE® II breath-actuated nebulizer ("AEII" or "AEII BAN") available from Trudell Medical International of London, Canada.

Baffle disc diameter (i.e., diverter surface area) and liquid volume (i.e., the aggregate volume between the outer tubular member and the inner tubular member including channels, gaps, passageways, or slots) are key components to nebulizer performance. Varying the size of the baffle disc diameter and liquid volume can directly affect aerosol output rate, without negatively impacting particle size (e.g., Mass Median Aerodynamic Diameter, or "MMAD") and the range of particles respirable deep into the respiratory system (e.g., the percentage of aerosol particle population less than 4.7 μm, or "%<4.7 μm"). With a smaller baffle disc diameter and a larger liquid volume, the aerosol output rate is shown to be greatly improved, especially when the nebulizer is utilized at lower air supply pressures, such as those seen on a home care compressor.

Testing has shown that a smaller baffle disc diameter provides a greater aerosol output rate than a larger baffle diameter. These results are unexpected and counterintuitive because normal expectations are that a larger vacuum would be provided by a larger baffle disc, and that the larger the baffle disc, the greater the pull on the liquid, thus resulting in a higher output rate. Normal expectations are also that a larger baffle disc would provide better aerosolization since the larger baffle offers more diverter surface area for break-up of liquid. Additionally, normal expectations are that a larger baffle provides more opportunity for particle impaction and aerosolization.

Testing has also shown that an increase in liquid volume, for example, by increasing liquid cylinder cross sectional area (La, by increasing the annular gap between the liquid cylinder and gas nozzle), or by adding additional channels or passageways or slots, will increase aerosol output rate. These results are also unexpected and counterintuitive because normal expectations are that a larger liquid cylinder cross-sectional area would require stronger negative pressure to draw up the liquid for aerosolization, and hence a larger baffle would be thought to be required for a larger liquid cylinder cross-sectional area. Normal expectations are also that a larger liquid cylinder cross-sectional area would result in larger residual volume.

Figure 4:
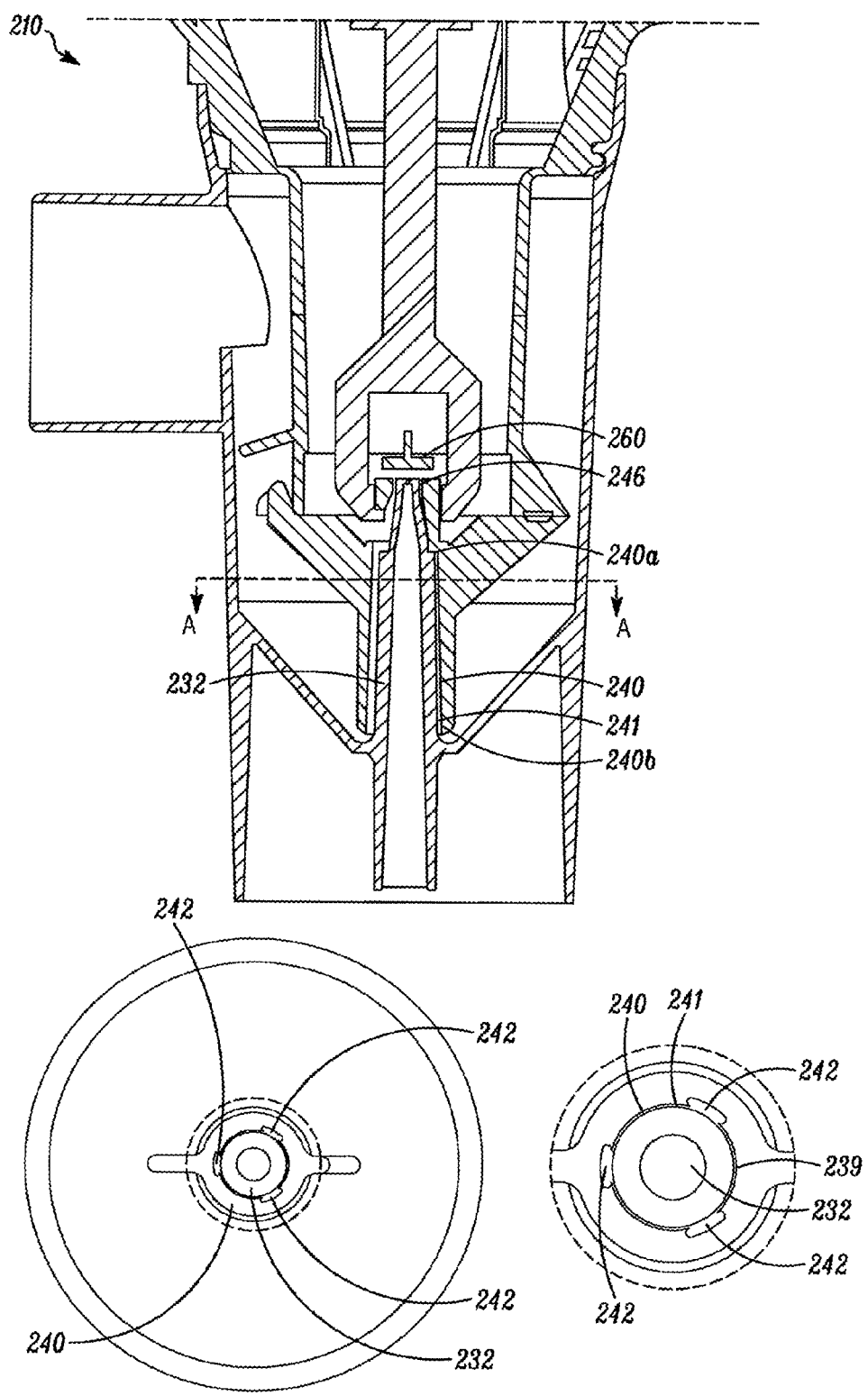
FIG. 4 is a cross-sectional side view of a second embodiment of a nebulizer.

Turning to FIG. 4, a cross-sectional view of a nebulizer 210 is shown with components and dimensions representative of those found in the AEROECLIPSE® II breath-actuated nebulizer. The nebulizer 210 of FIG. 4 may be described as a nebulizer having a fixed baffle 260 and a liquid orifice 246 or portion thereof that is moveable, such as those described in U.S. Pat. No. 6,929,003. In this embodiment, the nebulizer 210 has a baffle disc diameter of Ø4.20 mm (or a diverter surface area of 13.85 mm$^2$), a liquid outlet orifice 246 diameter of Ø2.52 mm, a liquid cylinder diameter of Ø5.55 mm at the top end 240*a* of the liquid cylinder 240, a liquid cylinder diameter of Ø6.54 mm at the bottom end 240*b* of the liquid cylinder 240, three additional liquid channels or slots 242 of 0.44 mm formed in the wall 239 of the liquid cylinder 240, and a liquid gap 241 of 0.15 mm formed between the outer tubular member, or the liquid cylinder 240, and the inner tubular member, or the gas nozzle 232. This nebulizer 210 has an equivalent liquid volume of 55 mm$^3$.

Figure 5:
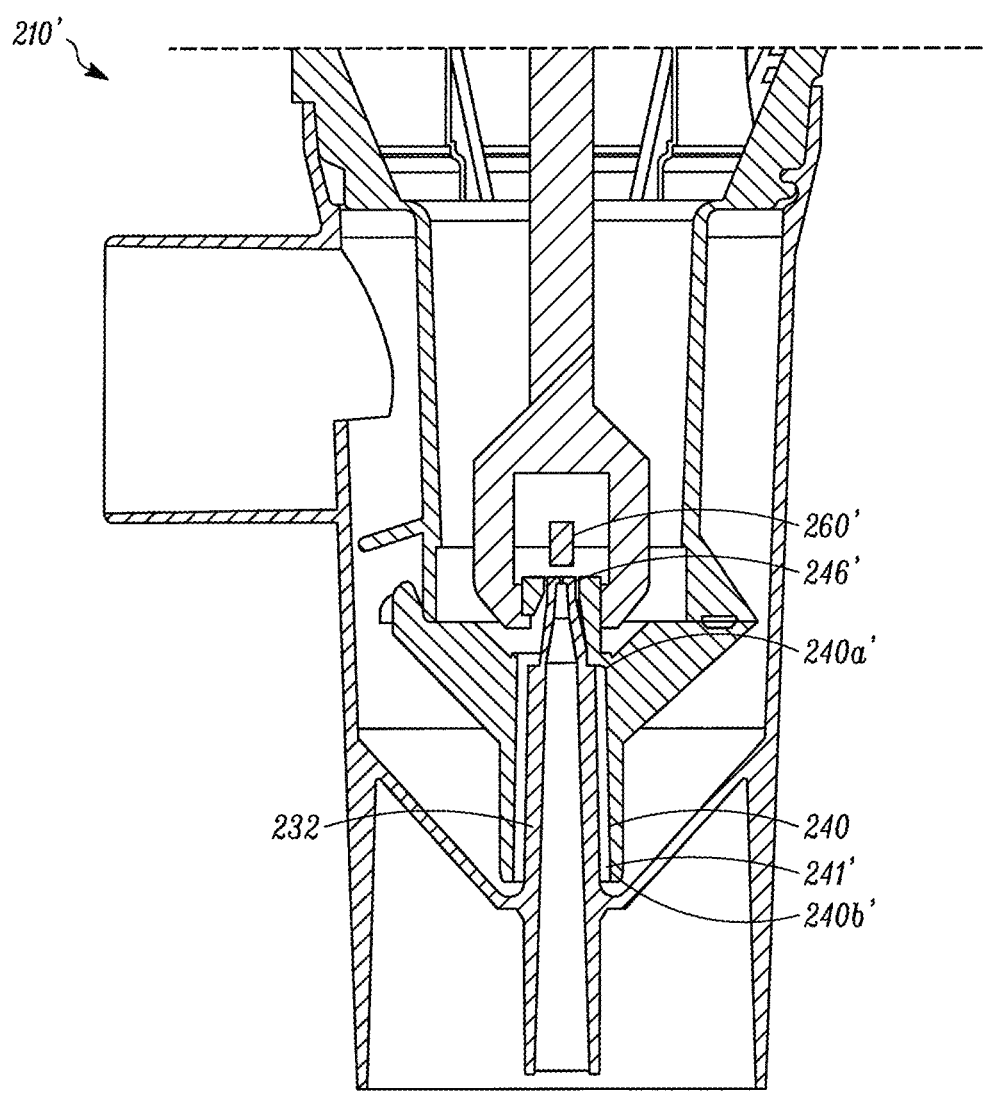
FIG. 5 is a cross-sectional side view of the nebulizer of FIG. 4 with particular dimensions modified to improve performance of the nebulizer.

FIG. 5 is a cross-sectional view of the nebulizer 210 of FIG. 4 with particular dimensions modified to improve performance of the nebulizer 210. The dimensions shown in the embodiment of FIG. 5 are considered preferred dimensions in that they are believed to provide optimal performance of the nebulizer. In this embodiment, a nebulizer 210' has a baffle 260' with a baffle disc diameter of Ø1.50 mm (or a diverter surface area of 1.77 mm$^2$), a liquid outlet orifice 246' diameter of Ø2.52 mm, a liquid cylinder diameter of Ø7.00 mm at the top end 240a' of the liquid cylinder 240, a liquid cylinder diameter of Ø7.98 mm at the bottom end 240b' of the liquid cylinder, no additional liquid channels or slots, and a liquid gap 241' of 0.88 mm formed between the outer tubular member, or the liquid cylinder 240, and the inner tubular member, or the gas nozzle 232. This nebulizer has an equivalent liquid volume of 286 mm$^3$.

Figure 6:
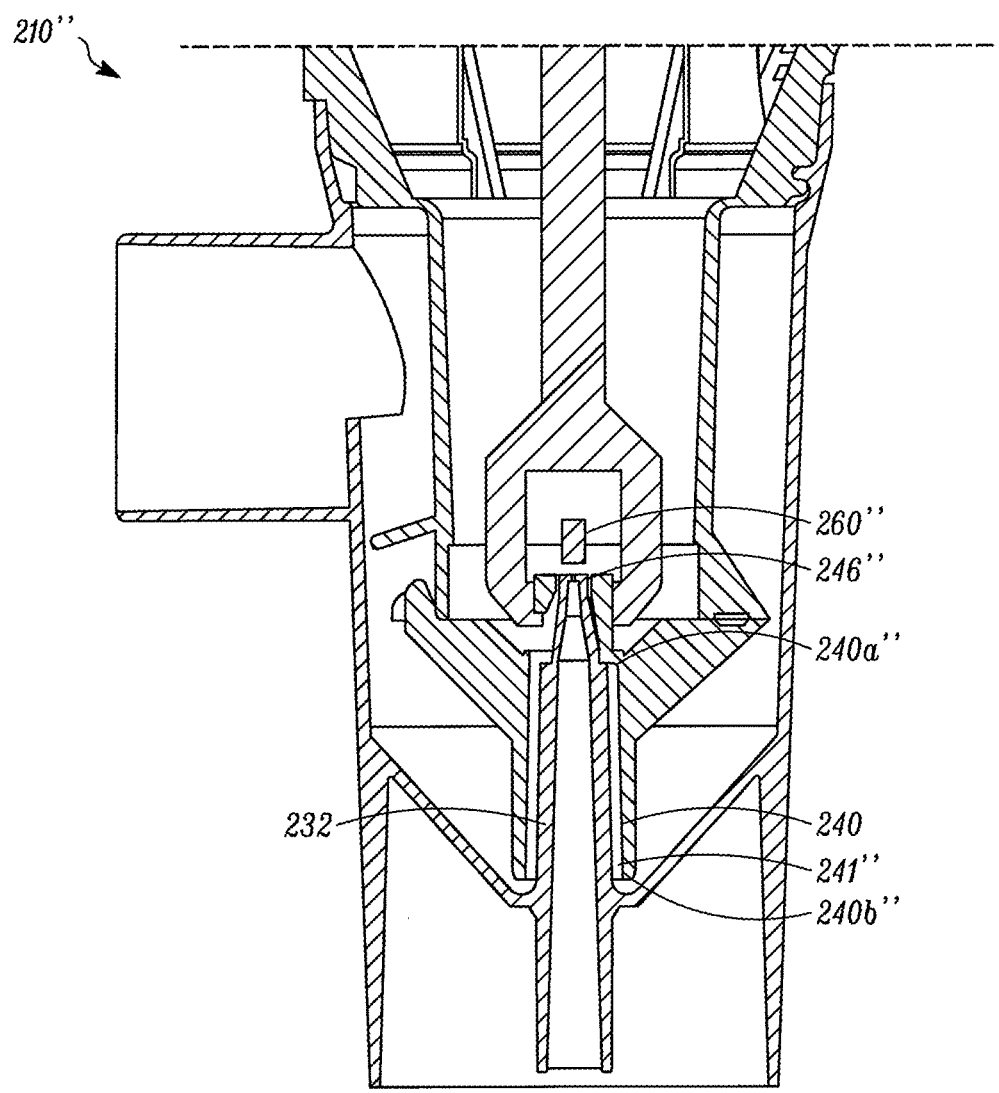
FIG. 6 is another cross-sectional side view of the nebulizer of FIG. 4 with ranges of particular dimensions intended to improve performance of the nebulizer.

FIG. 6 is a cross-sectional side view of the 210 nebulizer of FIG. 4 showing ranges of particular dimensions intended to enhance performance of the nebulizer 210. The ranges of dimensions shown in FIG. 6 are alternative dimensions that are intended to result in improved performance of the nebulizer. For example, a nebulizer 210" may have a baffle 260" with a baffle disc diameter of Ø1.00 mm to Ø2.50 mm (or a diverter surface area of 0.79 mm$^2$ to 4.91 mm$^2$), a liquid outlet orifice 246" diameter of Ø2.22 mm to Ø4.50 mm, a liquid cylinder diameter of Ø5.50 mm to Ø9.00 mm at the top end 240a" of the liquid cylinder 240, a liquid cylinder diameter of Ø6.50 mm to Ø10.00 mm at the bottom end 240b" of the liquid cylinder, no additional liquid channels or slots, and a liquid gap 241" of 0.40 mm to 2.00 mm formed between the outer tubular member, or the liquid cylinder 240, and the inner tubular member, or the gas nozzle 232. This nebulizer may have a range of equivalent liquid volume of 80 mm$^3$ to 1000 mm$^3$.

Figure 7:
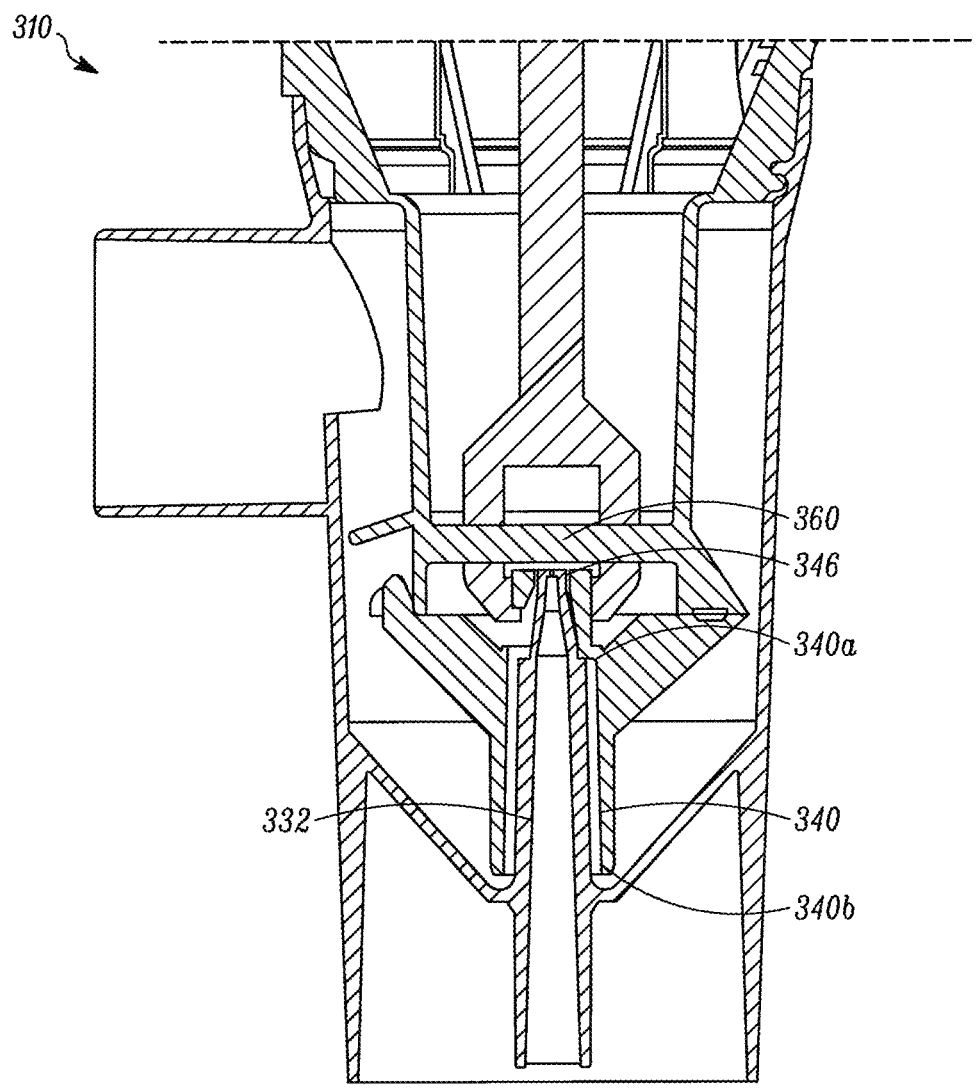
FIG. 7 is cross-sectional side view of a third embodiment of a nebulizer with ranges of particular dimensions intended to improve performance of the nebulizer.

FIG. 7 is cross-sectional side view of another embodiment of a nebulizer 310 shown with ranges of particular dimensions intended to enhance performance of the nebulizer 310. The nebulizer 310 of FIG. 7 is like the nebulizer 210 of FIG. 4 in that it may be described as a nebulizer having a fixed baffle 360 and a liquid orifice 346 or portion thereof that is moveable, similar to those described in U.S. Pat. No. 6,929, 003. However, the nebulizer 310 of FIG. 7 has a baffle 360 in the shape of a rib having a diverter surface area that covers at least 50% of the liquid outlet orifice 346. This embodiment also has a liquid outlet orifice diameter of Ø2.22 mm to Ø4.50 mm, a liquid cylinder diameter of Ø5.50 mm to Ø9.00 mm at the top end 340a of the liquid cylinder 340, a liquid cylinder diameter of Ø6.50 mm to 10.00 mm at the bottom end 340b of the liquid cylinder 340, no additional liquid channels or slots, and a liquid gap of 0.40 mm to 2.00 mm formed between the outer tubular member, or the liquid cylinder 340, and the inner tubular member, or the gas nozzle 332. This nebulizer 310 may have a range of equivalent liquid volume of 80 mm$^3$ to 1000 mm$^3$.

FIG. 8 is a cross-sectional side view of another embodiment of a nebulizer 410 with ranges of particular dimensions intended to enhance performance of the nebulizer 410. Specifically, the nebulizer of FIG. 8 may have a baffle 460 with a baffle disc diameter of Ø1.00 mm to Ø2.50 mm (or a diverter surface area of 0.79 mm$^2$ to 4.91 mm$^2$), a liquid outlet orifice 446 diameter of Ø2.52 mm to Ø4.50 mm, and one or more liquid channels 442 formed in the wall 439 of the liquid cylinder 440 of a quantity and size that results in an equivalent liquid volume of 80 mm$^3$ to 1000 mm$^3$. The nebulizer 410 of FIG. 8 omits the liquid gap formed between the outer tubular member, or the liquid cylinder 440, and the inner tubular member, or the gas nozzle 432.

Figure 9:
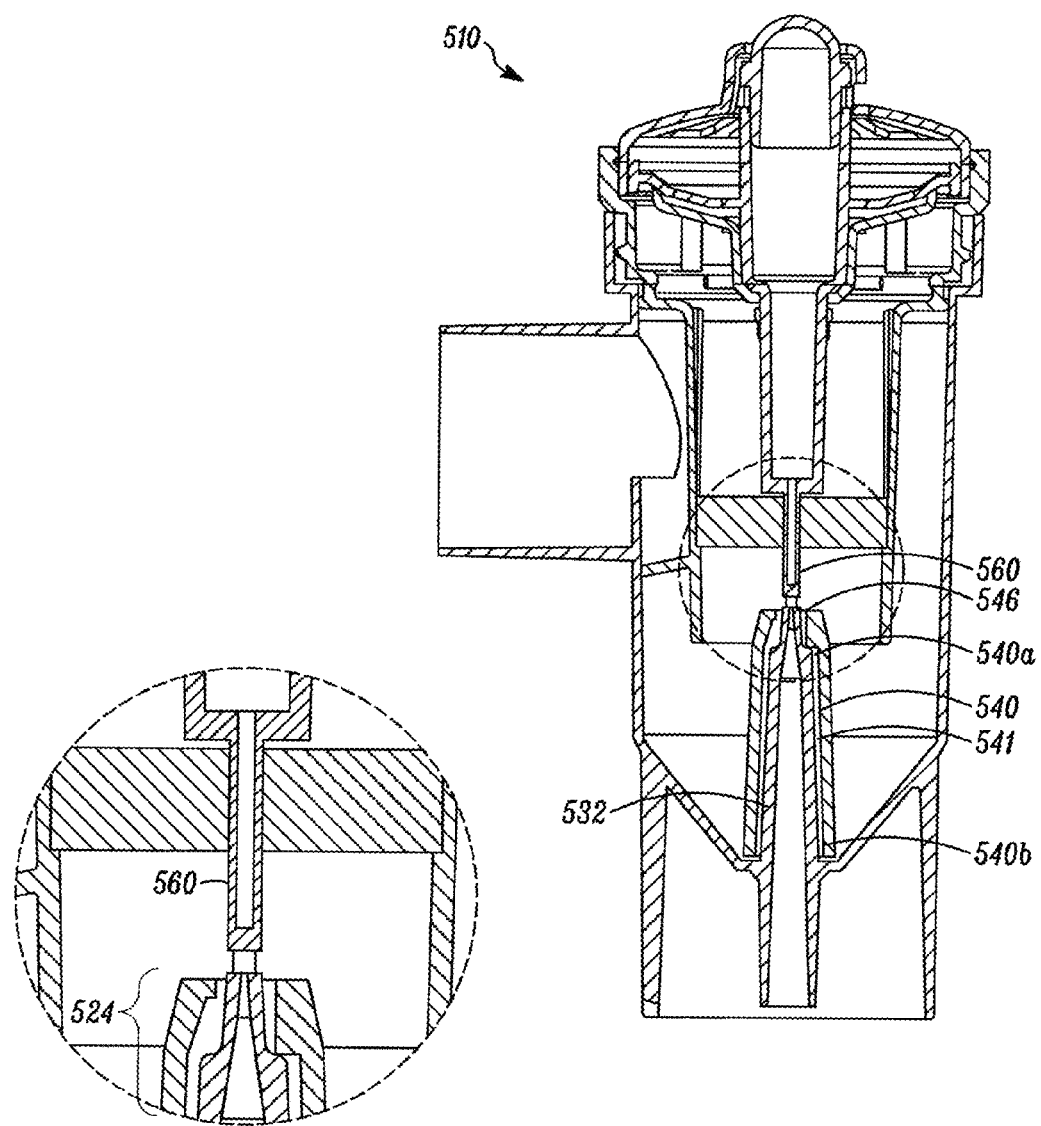
FIG. 9 is a cross-sectional side view of a fifth embodiment of a nebulizer with particular dimensions intended to improve performance of the nebulizer.

FIG. 9 is a cross-sectional side view of another commercial nebulizer 510 modified with ranges of particular dimensions intended to enhance performance of the nebulizer 510. The nebulizer 510 of FIG. 9 may be characterized as having a moveable baffle 560 and a fixed nozzle assembly 524, such as those described in U.S. Pat. Nos. 5,823,179 and 6,044, 841. In this embodiment, the nebulizer 510 may have a moveable baffle disc diameter of Ø1.00 mm to Ø2.50 mm (or a diverter surface area of 0.79 mm$^2$ to 4.91 mm$^2$), a liquid outlet orifice 546 diameter of Ø2.25 mm to Ø4.50 mm, a liquid cylinder diameter of Ø5.50 mm to Ø9.00 mm at the top end 540a of the liquid cylinder 540, a liquid cylinder diameter of Ø6.50 mm to 10.00 mm at the bottom end 540b of the liquid cylinder 540, no additional liquid channels or slots, and a liquid gap 541 formed between the outer tubular member, or the liquid cylinder 540, and the inner tubular member, or the gas nozzle 532, such that the device has an equivalent liquid volume of 80 mm$^3$ to 1000 mm$^3$.

The combined effect of baffle size and liquid volume/ liquid cylinder cross sectional area on aerosol output rate is shown in FIG. 10 at various air supply pressures. In FIG. 10, an AEII BAN device modified with a baffle disc diameter of Ø3.50 mm, and with existing liquid volume/liquid channel dimensions, was filled with nebulizer solution (albuterol) and aerosolized for 2 minutes continuously (dial set to continuous mode) while an inhalation flow of 28.3 lpm was applied. The drug was collected onto a filter and assayed. The total amount of drug collected in 2 minutes was then determined and divided in half to obtain the output per minute. This was done for air supply pressures of 15 psi, 20 psi, and 50 psi. Next, the baffle disc diameter of the AEII BAN was reduced to Ø1.50 mm and the cross-sectional area of the AEII BAN liquid cylinder increased by 50%, which resulted in an increased liquid volume. This device combination was then tested using the 2-minute continuous drug output test method described above. Results show that the reduced baffle disc diameter and the increased liquid volume/liquid cylinder cross-sectional area have greater aerosol performance—in this particular test, improving aerosol output rate at the lower air supply pressures of 15 psi and 20 psi by as much as 75%, and by approximately 10% at the higher air supply pressure of 50 psi.

In FIG. 11, similar two-minute continuous drug output testing was conducted, but in this testing, the effect of baffle size alone on aerosol output rate was determined for given liquid cylinder cross-sectional areas. First, an AEII BAN device was modified with a small baffle diameter (Ø1.50 mm) and then a large baffle diameter (Ø3.50 mm) and tested using the 2-minute continuous drug output testing previously described. For the same liquid volume/liquid cylinder cross-sectional area, aerosol output rate was shown to decrease with an increase in baffle diameter. Next, the AEII BAN liquid cylinder cross sectional area was increased by 50%. This larger liquid cylinder cross sectional area was then combined with the same two baffle diameter sizes of Ø1.50 mm and Ø3.50 mm. Again, 2-minute continuous drug output test results showed a decrease in aerosol output rate with an increase in baffle diameter.

Further investigation into the effect of baffle size and liquid volume/liquid cylinder cross sectional area on aerosol output rate was conducted by testing various baffle sizes in combination with various liquid cylinder cross sectional areas under simulated breathing conditions. An ASL5000 Test Lung was set up for this testing with the following test parameters: Tidal Volume: 600 mL, I:E ratio 1:2, BPM 10. A 5 lpm air supply was applied to the nebulizer as the driving gas. The following nebulizer combinations were tested:

| Liquid Channel/Cylinder<br>Cross-Sectional Area | Baffle Diameter<br>(mm) |
|---|---|
| AeroEclipse II Current Production Device | 4.20 |
| 36% Increase in AEII liquid cylinder cross sectional area | 1.50<br>3.50 |
| 50% Increase in AEII liquid cylinder cross sectional area | 1.50<br>3.50 |
| 135% Increase in AEII liquid cylinder cross sectional area | 1.50<br>3.50 |

Each device was first particle size tested using a Malvern Spraytech Unit to obtain MMAD particle size data and %<4.7 μm. Each nebulizer combination listed above was then filled with 3 mL of nebulizer solution and placed on the breathing simulator apparatus. The devices were tested with the dial set to continuous mode. A bacterial filter was placed at the nebulizer outlet to capture the aerosol. Each device was run until "sputter" and bacterial filters were changed every minute. Filters were assayed for total amount collected on each filter. Respirable amount was calculated by multiplying the total amount collected on the filter by the %<4.7 μm. This equates to the respirable output per minute.

FIG. 12 shows the effect of baffle size on aerosol output rate for a preferred liquid volume/liquid cylinder cross sectional area of a 50% increase in AEII liquid cylinder cross sectional area. Results show that for a nebulizer device with the same liquid cylinder cross sectional area, aerosol output rate improves with the smaller baffle diameter. In this particular test, aerosol output rate increased by approximately 23% going from the larger Ø3.5 mm baffle to the smaller Ø1.5 mm baffle.

Figure 13:
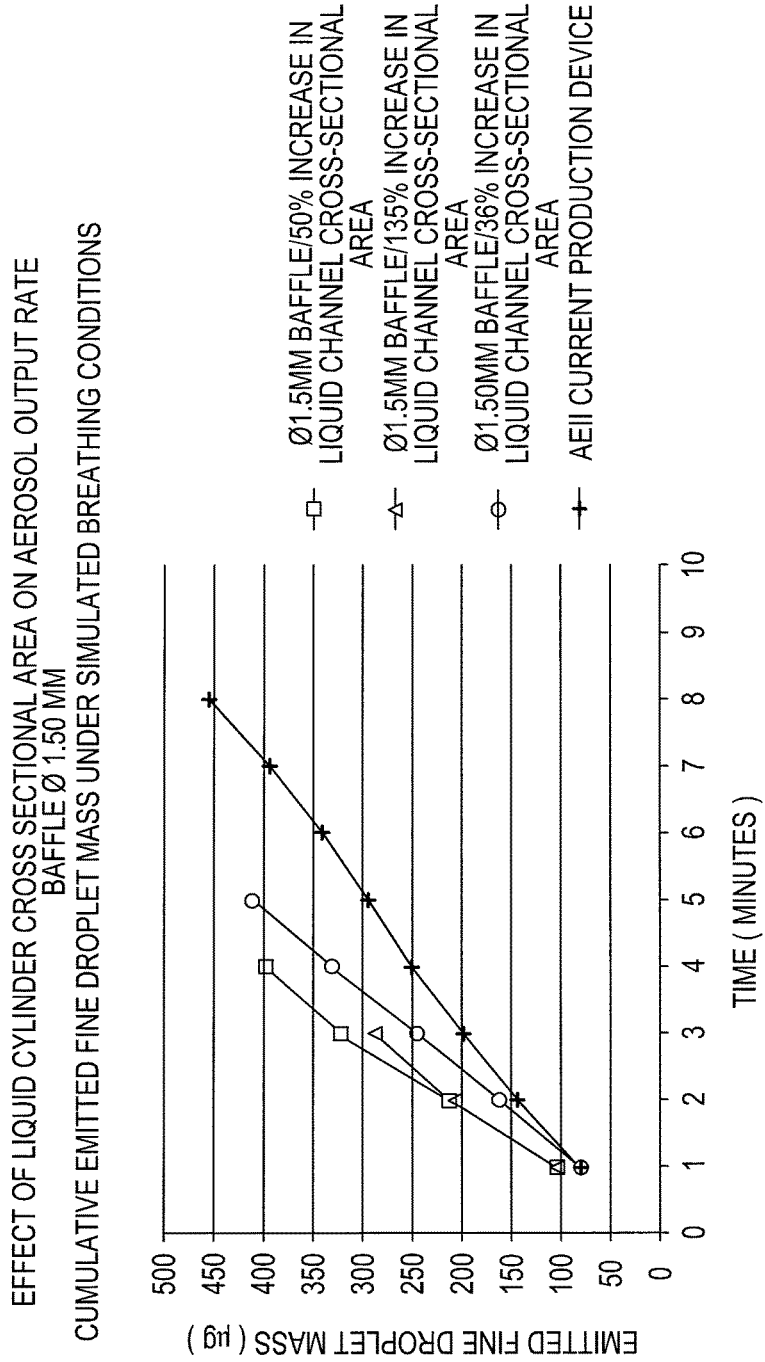
FIG. 13 is a graph comparing aerosol output rates for additional tests performed on the nebulizer of FIG. 4 and modified versions thereof.
Figure 14:
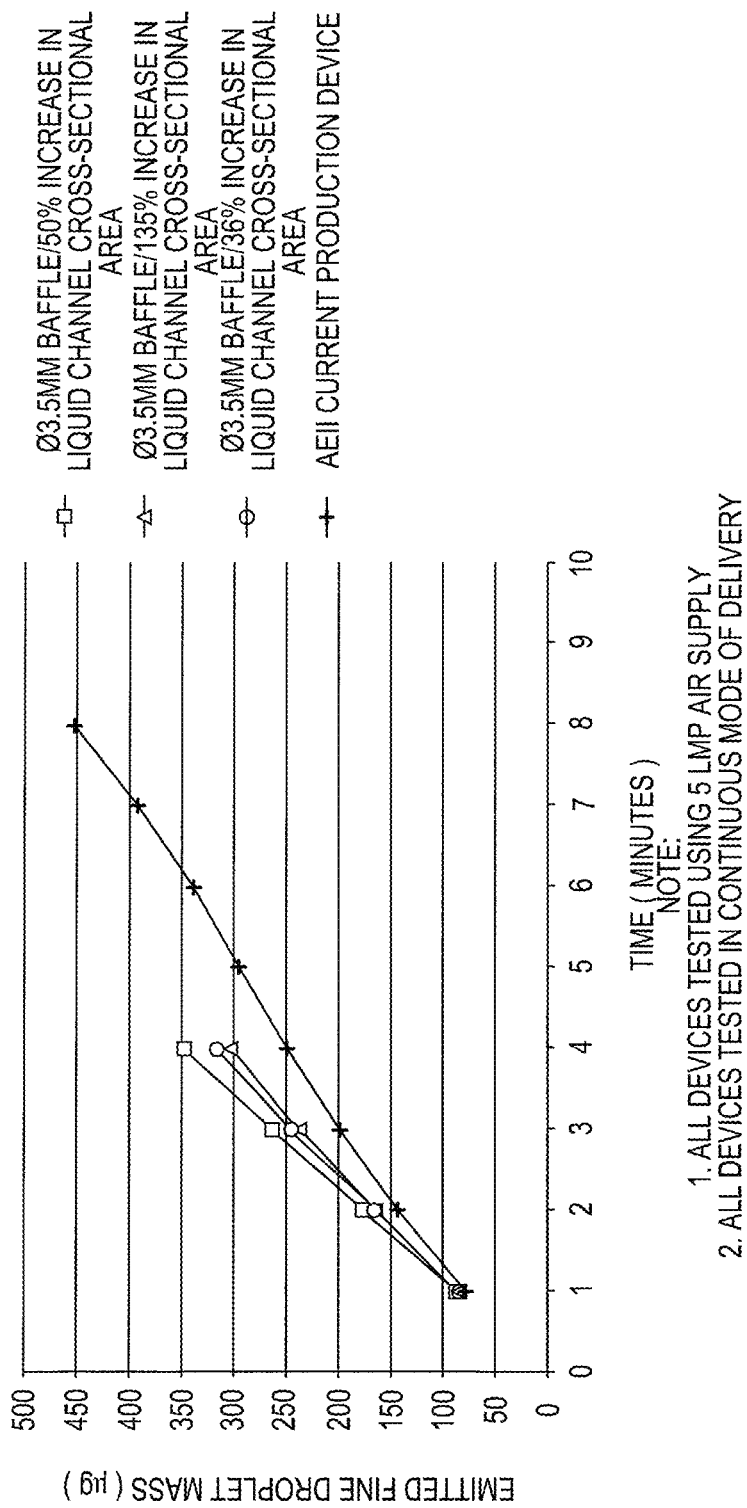
FIG. 14 is a graph comparing aerosol output rates for further tests performed on the nebulizer of FIG. 4 and modified versions thereof.

The effect of liquid volume/liquid cylinder cross sectional area on aerosol output rate can be seen in FIGS. 13 and 14. For a given baffle diameter, the cumulative respirable aerosol output is plotted over time (output rate) for the various liquid cylinder cross sectional areas tested. In FIG. 13, the baseline device for comparison purposes was the current AEII BAN device. Results show that for a baffle size of Ø1.50 mm, aerosol output rate increases with an increase in liquid cylinder cross sectional area. In this particular test, aerosol output rate increased from the baseline device by 83% to 89% for increases in liquid cylinder cross sectional area of 135% and 50% respectively. An increase in aerosol output rate of approximately 45% was seen with the increase in liquid cylinder cross sectional area of 36%. Another important aspect seen from the test results is the decrease in delivery time. That is to say, delivery time decreases as the size of the liquid cylinder cross sectional area increases.

Increased aerosol output rate and decreased delivery time are significant from a therapeutic standpoint because it means more medication can be delivered quickly, for example, in the event of an asthmatic episode. It also means less treatment time for a patient—with more medication being delivered per minute, the patient can receive the required dosage in less time. This is important since a patient's time is valuable and many patients may forgo their treatment if the treatment time is too long. By improving the aerosol output rate and decreasing delivery time, patients may be more likely to complete their treatments, which may prevent asthmatic episodes, and as result, reduce trips to the hospital.

FIG. 14 shows the effect of liquid volume/liquid cylinder cross sectional area on aerosol output rate for a baffle disc diameter of Ø3.5 mm. The results from FIG. 14 again show an increase in aerosol output rate with increase in liquid cylinder cross sectional area. The results also shows a decrease in aerosol output rate compared to FIG. 13, where the only difference is the smaller baffle diameter size (Ø1.5 mm). Looking strictly at the effect of liquid cylinder cross sectional area on the Ø3.5 mm baffle, output rate increased compared to the baseline device of this group (Ø4.2 mm Baffle/Current AEII BAN device) anywhere from 35% to 40% for the various sized liquid cylinder cross sectional areas. Comparing results to those in FIG. 13, aerosol output rate for the larger baffle Ø3.5 mm decreased by 20% to 26% for increases in liquid cylinder cross sectional areas of 50% and 135% respectively, and 3% for the increase in liquid cylinder cross sectional area of 36%. Again, delivery time is shown to decrease with an increase in liquid channel cross sectional area relative to the baseline AEII device.

Figure 16:
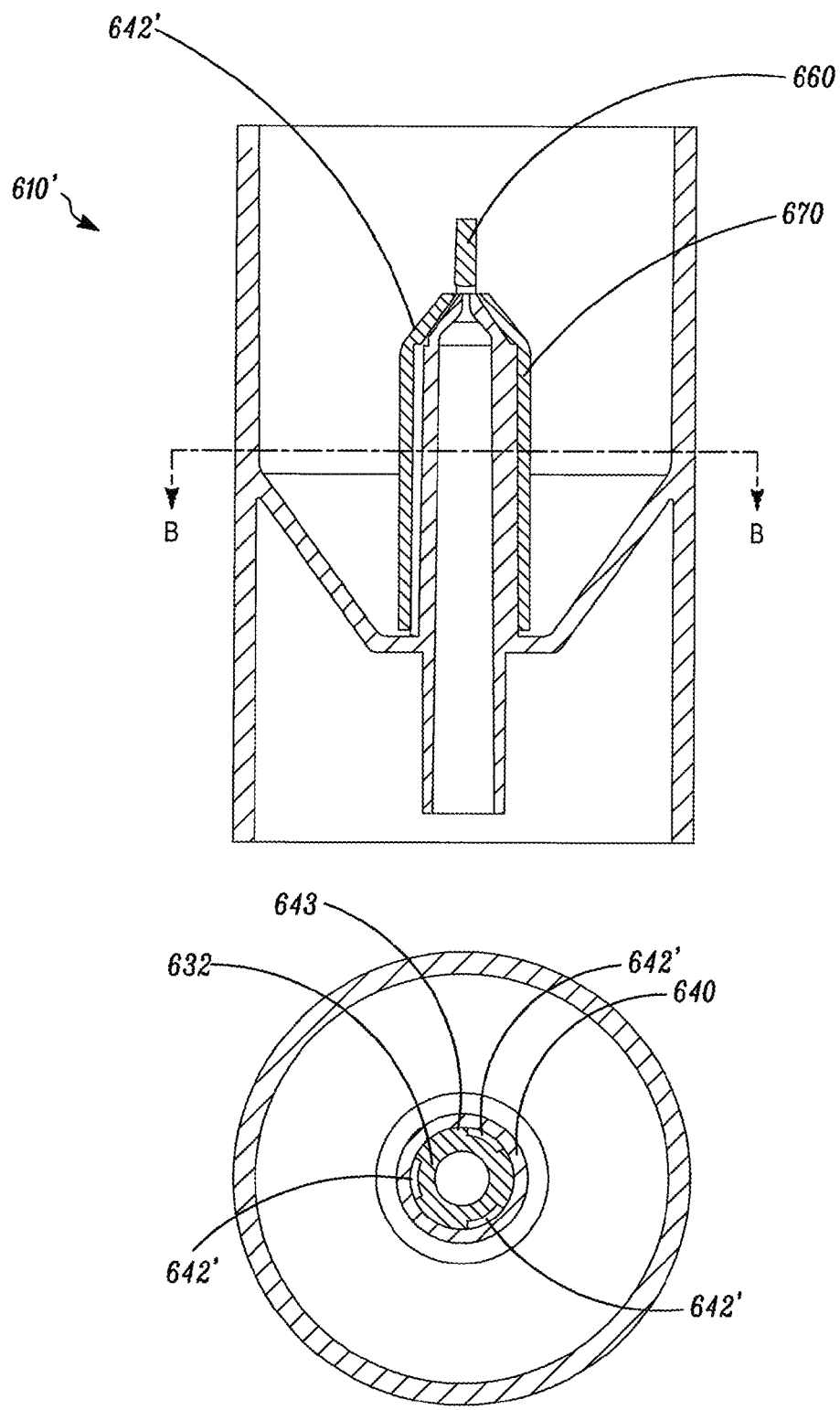
FIG. 16 is a cross-sectional side view of the nebulizer of FIG. 15 with particular dimensions modified to improve performance of the nebulizer.
Figure 18:
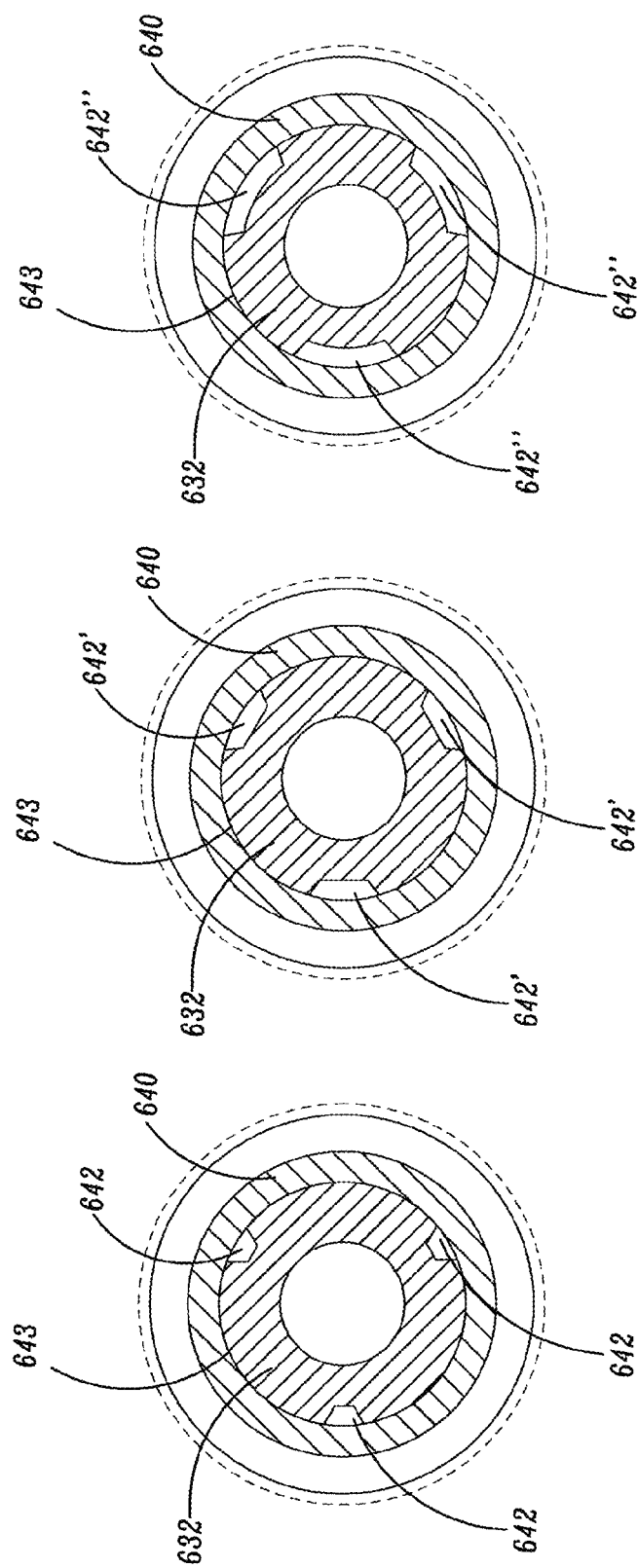
FIG. 18 is a cross-sectional top view of the nebulizers of FIGS. 15-17 comparing particular dimensions; and, FIG. 19 is a graph comparing the aerosol output rates for the nebulizers of FIGS. 15-17.

The effect of a small baffle size and liquid volume/liquid channel cross sectional area can also be seen on the aerosol output rate of another commercially available nebulizer. As shown in the cross-sectional views of FIGS. 15-17, another commercially available nebulizer 610 was tested along with several modified versions of that device. The nebulizer 610 of FIG. 15 may be described as having a fixed baffle 660 and a fixed nozzle cover 670 with a plurality of liquid channels 642 formed in the outer wall 643 of the air supply post or inner nozzle 632. The nebulizer of FIG. 15 omits any liquid gap formed between the outer tubular member, or the liquid cylinder 640, and the inner tubular member, or the gas nozzle 632. The modified versions of that device 610' involved an increase in the cross-sectional area of the liquid channels 642' to obtain an overall 60% increase in volume of the liquid channels 642', as seen in FIG. 16, and then decreasing the cross sectional area of the liquid channels 642" to obtain an overall 10% reduction in volume of the liquid channels 642", as seen in the device 610" of FIG. 17. The liquid channels 642, 642', and 642" of the nebulizers of FIG. 15-17 are compared in FIG. 18.

Testing of these nebulizers was conducted on the ASL5000 breathing simulator, using the same parameters as previously described for the AEII nebulizer modifications discussed in FIGS. 13 and 14. Furthermore, a 6 lpm air supply was provided to the nebulizer as the driving gas. Test results of the baseline nebulizer shown in FIG. 15 and modified versions shown in FIGS. 16 and 17 are presented in FIG. 19. These test results confirm that aerosol output rate can be affected by liquid channel cross sectional area (and hence liquid channel volume)—a small baffle diameter combined with a large liquid channel cross sectional area provides an increase in aerosol output rate. In the case of the commercially available nebulizer of FIG. 15, increasing the liquid channel volume by 60% resulted in an increase in aerosol output rate of approximately 50%. Decreasing the liquid channel volume by 10% resulted in a decrease in aerosol output rate of approximately 3%. Also important to note, aerosol delivery time decreased with the increase in liquid channel volume and increased with the decrease in liquid channel volume. This is consistent with test results for the modified AEII nebulizer testing.

The results detailed herein are significant because they indicate that both baffle diameter and liquid volume/liquid cylinder cross sectional area impact aerosol output rate and aerosol delivery time, while not negatively affecting particle size. By combining a small baffle disc diameter with various sizes of liquid volume/liquid cylinder cross sectional area, the nebulizer aerosol output rate and delivery time can be optimized for maximum benefit to the end user. The nebulizer could be optimized for treatment by the patient at home or for treatment in a hospital, depending on the requirements. For example, the objective may be to provide a nebulizer treatment at home to an end user with a hectic daily life, and thus to provide a given amount of medication to the end user in as short a time as possible in order not to disrupt the end user's busy schedule. The nebulizer for this application could be a combination of a small baffle disc diameter (e.g., Ø1.50 mm) with a large liquid channel size (e.g., 50% increase in AEII liquid cylinder cross sectional area). Alternatively, the nebulizer application may be treatment in a hospital for delivery of a medication requiring a longer delivery time (for instance due to drug potency). In this case, the nebulizer for this application may be a slightly larger baffle disc diameter (e.g., Ø2.50 mm) with a slightly smaller liquid channel size (e.g., 25% increase in AEII liquid cylinder cross sectional area). In other words, depending on the patient requirements and the driving gas pressure to be utilized with the device (e.g., homecare compressor or hospital wall air supply), the appropriate combination of baffle disc diameter and liquid channel size could be selected in order to provide the most effective nebulizer treatment to the end user.

The above nebulizer embodiments have been described for use in medical or therapeutic applications. It is intended that the foregoing detailed description be regarded as illustrative rather than limiting, and that it be understood that the following claims, including all equivalents, are intended to define the scope of this invention.

I claim:

1. A nebulizer comprising:

a housing having a chamber for holding an aerosol;

an air outlet communicating with the chamber for permitting the aerosol to be withdrawn from the chamber;

a reservoir for holding a liquid to be aerosolized;

a liquid orifice located in the chamber;

one or more liquid channels defined between the reservoir and the liquid orifice, the one or more liquid channels having a liquid volume;

a pressurized gas outlet located in the chamber adjacent to the liquid orifice and positioned to deliver a flow of pressurized gas into the chamber; and, a baffle located in the chamber and positioned relative to the pressurized gas outlet and the liquid orifice so as to divert pressurized gas from the pressurized gas outlet and over the liquid orifice, the baffle having a diverter surface area;

wherein the pressurized gas is delivered at a flow rate of 3-5 liters per minute (lpm);

wherein the liquid volume is at least 80 $mm^3$; and, wherein the diverter surface area is less than 5.0 $mm^2$.

2. The nebulizer of claim 1, wherein the liquid volume is less than 1000 $mm^3$.

3. The nebulizer of claim 1, wherein the diverter surface area is greater than 0.75 $mm^2$.

4. The nebulizer of claim 1, wherein the liquid volume is between 250 $mm^3$ and 300 $mm^3$.

5. The nebulizer of claim 1, wherein the diverter surface area is between 1.5 $mm^2$ and 2.0 $mm^2$.

6. The nebulizer of claim 1, wherein the baffle has a disc-shaped diverter surface area.

7. The nebulizer of claim 1, wherein the baffle is shaped as a rib.

8. The nebulizer of claim 6, wherein the disc-shaped diverter surface area has a diameter between 1.0 mm and 2.5 mm.

9. The nebulizer of claim 1, wherein the diverter surface area of the baffle is at least 50% of a cross-sectional area of the liquid orifice.

10. The nebulizer of claim 1, wherein the liquid orifice is positioned at a distal end of a first nozzle extending in to the chamber, and the pressurized gas outlet is positioned at a distal end of a second nozzle extending in to the chamber through the first nozzle.

11. The nebulizer of claim 10, wherein the one or more liquid channels are formed between the first nozzle and the second nozzle.

12. The nebulizer of claim 1, wherein the baffle is moveable relative to the pressurized gas outlet and the liquid outlet between a nebulizing position and a non-nebulizing position.

13. The nebulizer of claim 1, wherein at least one portion of the liquid orifice is moveable between a nebulizing position and a non-nebulizing position.

14. The nebulizer of claim 1, wherein the pressurized gas is delivered at pressures in the range of 15 to 30 pounds per square inch (psi).

15. The nebulizer of claim 1, wherein the pressurized gas is delivered by a home care compressor.

16. The nebulizer of claim 1, wherein the pressurized gas outlet is connectable with a home care compressor.

17. The nebulizer of claim 1, wherein the nebulizer delivers aerosolized particles less than 4.7 micrometers (μm).

* * * * *